US011237230B1

(12) United States Patent
Iwasaki et al.

(10) Patent No.: US 11,237,230 B1
(45) Date of Patent: Feb. 1, 2022

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Nerima Tokyo (JP); Satoshi Shirotori, Yokohama Kanagawa (JP); Akira Kikitsu, Yokohama Kanagawa (JP); Yoshihiro Higashi, Komatsu Ishikawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 17/169,388

(22) Filed: Feb. 5, 2021

(30) Foreign Application Priority Data

Sep. 14, 2020 (JP) .............................. JP2020-153915

(51) Int. Cl.
| | | |
|---|---|---|
| *G01R 33/09* | (2006.01) | |
| *G01R 15/20* | (2006.01) | |
| *G01N 27/90* | (2021.01) | |
| *G01R 19/00* | (2006.01) | |
| *G01R 31/382* | (2019.01) | |
| *A61B 5/243* | (2021.01) | |
| *A61B 5/245* | (2021.01) | |

(52) U.S. Cl.
CPC .......... *G01R 33/093* (2013.01); *G01N 27/90* (2013.01); *G01R 15/205* (2013.01); *G01R 19/0092* (2013.01); *G01R 31/382* (2019.01); *A61B 5/243* (2021.01); *A61B 5/245* (2021.01)

(58) Field of Classification Search
CPC .. G01R 31/382; G01R 15/205; G01R 33/093; G01R 19/0092; G01N 27/90
See application file for complete search history.

(56) References Cited

U.S. PATENT DOCUMENTS

| | | |
|---|---|---|
| 5,729,137 A | 3/1998 | Daughton et al. |
| 6,025,979 A | 2/2000 | Yamane et al. |
| 2018/0271395 A1 | 9/2018 | Iwasaki et al. |
| 2019/0293735 A1 | 9/2019 | Ushioda et al. |
| 2019/0369172 A1 | 12/2019 | Kikitsu et al. |

FOREIGN PATENT DOCUMENTS

| | | |
|---|---|---|
| JP | H11-101861 A | 4/1999 |
| JP | 2018-155719 A | 10/2018 |
| JP | 2019-207167 A | 12/2019 |
| WO | WO 2017/204151 A1 | 11/2017 |

*Primary Examiner* — Alesa Allgood
(74) *Attorney, Agent, or Firm* — Finnegan, Henderson, Farabow, Garrett & Dunner L.L.P.

(57) ABSTRACT

According to one embodiment, a magnetic sensor includes a sensor part, a first circuit, and a second circuit. The sensor part includes a magnetic element part, first and second conductive members. The magnetic element part includes first to fourth magnetic elements. The first conductive member includes first to third conductive portions, and first and second middle portions. The second conductive member includes fourth to sixth conductive portions, and third and fourth middle portions. The first circuit is electrically connected to the third and sixth conductive portions. The first circuit is configured to supply a first current between the third and sixth conductive portions. The second circuit is electrically connected to a first connection point and a second connection point. The second circuit is electrically connected to first and second connection points. The second circuit is configured to supply a second current between the first and second connection points.

20 Claims, 19 Drawing Sheets

MAGNETIC SENSOR AND INSPECTION DEVICE

CROSS-REFERENCE TO RELATED APPLICATIONS

This application is based upon and claims the benefit of priority from Japanese Patent Application No. 2020-153915, filed on Sep. 14, 2020; the entire contents of which are incorporated herein by reference.

FIELD

Embodiments described herein generally relate to a magnetic sensor and an inspection device.

BACKGROUND

There is a magnetic sensor that uses a magnetic layer. There is an inspection device that uses the magnetic sensor. It is desirable to increase the sensitivity of the magnetic sensor.

DETAILED DESCRIPTION

Figure 1A:
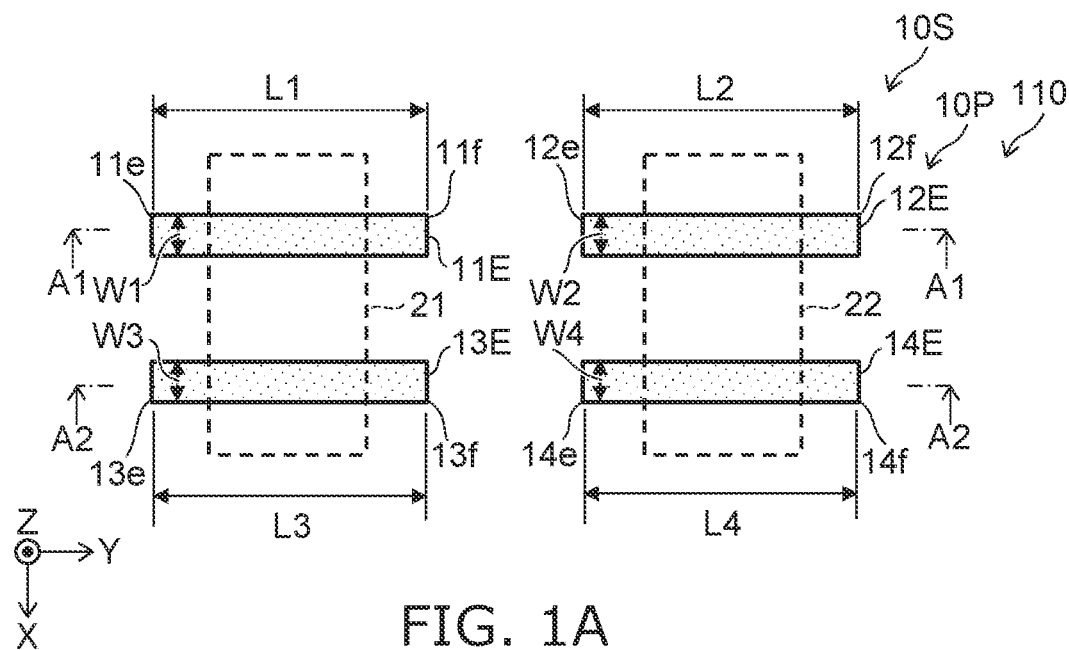
FIGS. 1A to 1C are schematic views illustrating a magnetic sensor according to a first embodiment.

According to one embodiment, a magnetic sensor includes a sensor part, a first circuit, and a second circuit. The sensor part includes a magnetic element part, a first conductive member, and a second conductive member. The magnetic element part includes a first magnetic element, a second magnetic element, a third magnetic element, and a fourth magnetic element. The first magnetic element includes a first element portion and a first element other-portion. The second magnetic element includes a second element portion and a second element other-portion. The third magnetic element includes a third element portion and a third element other-portion. The fourth magnetic element includes a fourth element portion and a fourth element other-portion. The first element other-portion is between the first element portion and the second element other-portion in a first direction. The second element portion is between the first element other-portion and the second element other-portion in the first direction. The third element other-portion is between the third element portion and the fourth element other-portion in the first direction. The fourth element portion is between the third element other-portion and the fourth element other-portion in the first direction. The first element other-portion is electrically connected to the second element portion. The third element other-portion is electrically connected to the fourth element portion. The first element portion is electrically connected to the third element portion. The second element other-portion is electrically connected to the fourth element other-portion. The first conductive member includes a first conductive portion, a second conductive portion, a third conductive portion, a first middle portion, and a second middle portion. A direction from the second conductive portion toward the first conductive portion is along a second direction crossing the first direction. The third conductive portion is between the first conductive portion and the second conductive portion. The first middle portion is between the first conductive portion and the third conductive portion. The second middle portion is between the third conductive portion and the second conductive portion. A direction from the first magnetic element toward the second middle portion is along a third direction crossing a plane including the first and second directions. A direction from the third magnetic element toward the first middle portion is along the third direction. The second conductive member includes a fourth conductive portion, a fifth conductive portion, a sixth conductive portion, a third middle portion, and a fourth middle portion. A direction from the fifth conductive portion toward the fourth conductive portion is along the second direction. The sixth conductive portion is between the fifth conductive portion and the fourth conductive portion. The third middle portion is between the fourth conductive portion and the sixth conductive portion. The fourth middle portion is between the sixth conductive portion and the fifth conductive portion. A direction from the second magnetic element toward the fourth middle portion is along the third direction. A direction from the fourth magnetic element toward the third middle portion is along the third direction. The first conductive portion is electrically connected to the fourth conductive portion. The second conductive portion is electrically connected to the fifth conductive portion. The first circuit is electrically connected to the third and sixth conductive portions. The first circuit is configured to supply a first current between the third conductive portion and the sixth conductive portion. The first current includes an alternating current component. The second circuit is electrically connected to a first connection point and a second connection point. The first connection point is between the first element portion and the third element portion. The second connection point is between the second element other-portion and the fourth element other-portion. The second circuit is configured to supply a second current between the first connection point and the second connection point.

According to one embodiment, a magnetic sensor includes a sensor part, a first circuit a second circuit. The sensor part includes a magnetic element part and a first conductive member. The magnetic element part includes a first magnetic element, a second magnetic element, a third magnetic element, and a fourth magnetic element. The first magnetic element includes a first element portion and a first element other-portion. The second magnetic element includes a second element portion and a second element other-portion. The third magnetic element includes a third element portion and a third element other-portion. The fourth magnetic element includes a fourth element portion and a fourth element other-portion. A direction from the first element portion toward the first element other-portion, a direction from the second element portion toward the second element other-portion, a direction from the third element portion toward the third element other-portion, and a direction from the fourth element portion toward the fourth element other-portion are along a first direction. The first element portion is electrically connected to the second element portion. The third element portion is electrically connected to the fourth element portion. The first element other-portion is electrically connected to the fourth element other-portion. The second element other-portion is electrically connected to the third element other-portion. The first conductive member includes a first conductive portion, a second conductive portion, a first portion, a second portion, a third portion, and a fourth portion. A position in a second direction of the first portion is between a position in the second direction of the first conductive portion and a position in the second direction of the second conductive portion. The second direction crosses the first direction. A position in the second direction of the second portion is between the position in the second direction of the first portion and the position in the second direction of the second conductive portion. A position in the second direction of the third portion is between the position in the second direction of the second portion and the position in the second direction of the second conductive portion. A position in the second direction of the fourth portion is between the position in the second direction of the third portion and the position in the second direction of the second conductive portion. A first orientation from the first magnetic element toward the first portion is along a third direction crossing a plane including the first and second directions. A second orientation from the second magnetic element toward the second portion is a reverse of the first orientation. A third orientation from the third magnetic element toward the third portion is a same as the first orientation. A fourth orientation from the fourth magnetic element toward the fourth portion is a reverse of the first orientation. The first circuit is electrically connected to the first and second conductive portions. The first circuit is configured to supply a first current between the first conductive portion and the second conductive portion. The first current includes an alternating current component. The second circuit is electrically connected to a first connection point and a second connection point. The first connection point is between the first element portion and the second element portion. The second connection point is between the third element portion and the fourth element portion. The second circuit is configured to supply a second current between the first connection point and the second connection point.

According to one embodiment, a magnetic sensor includes a sensor part, a first circuit, and a second circuit. The sensor part includes a magnetic element part and a first conductive member. The magnetic element part includes a first magnetic element, a second magnetic element, a third magnetic element, and a fourth magnetic element. The first magnetic element includes a first element portion and a first element other-portion. The second magnetic element includes a second element portion and a second element other-portion. The third magnetic element includes a third element portion and a third element other-portion. The fourth magnetic element includes a fourth element portion and a fourth element other-portion. A direction from the first element portion toward the first element other-portion, a direction from the second element portion toward the second element other-portion, a direction from the third element portion toward the third element other-portion, and a direction from the fourth element portion toward the fourth element other-portion are along a first direction. A second direction from the first magnetic element toward the fourth magnetic element crosses the first direction. A direction from the third magnetic element toward the second magnetic element is along the second direction. A direction from the third magnetic element toward the first magnetic element is along a third direction crossing a plane including the first and second directions. A direction from the second magnetic element toward the fourth magnetic element is along the third direction. The first element portion is electrically connected to the third element portion. The second element portion is electrically connected to the fourth element portion. The first element other-portion is electrically connected to the second element other-portion. The third element other-portion is electrically connected to the fourth element other-portion. The first conductive member includes a first conductive portion, a second conductive portion, a first middle portion, and a second middle portion. The first middle portion is between the first conductive portion and the second conductive portion in the second direction. The second middle portion is between the first middle portion and the second conductive portion in the second direction. The first middle portion is between the third magnetic element and the first magnetic element in the third direction. The second middle portion is between the second magnetic element and the fourth magnetic element in the third direction. The first circuit is electrically connected to the first and second conductive portions. The first circuit is configured to supply a first current between the first conductive portion and the second conductive portion. The first current includes an alternating current component. The second circuit is electrically connected to a first connection point and a second connection point. The first connection point is between the third element portion and the first element portion. The second connection point is between the second element portion and the fourth element portion. The second circuit is configured to supply a second current between the first connection point and the second connection point.

According to one embodiment, a magnetic sensor includes a sensor part, a first circuit, and a second circuit. The sensor part includes a magnetic element part, a first conductive member, and a second conductive member. The magnetic element part includes a first magnetic element, a second magnetic element, a third magnetic element, and a fourth magnetic element. The first magnetic element includes a first element portion and a first element other-portion. The second magnetic element includes a second element portion and a second element other-portion. The third magnetic element includes a third element portion and a third element other-portion. The fourth magnetic element includes a fourth element portion and a fourth element other-portion. A direction from the first element portion toward the first element other-portion, a direction from the second element portion toward the second element other-portion, a direction from the third element portion toward the third element other-portion, and a direction from the fourth element portion toward the fourth element other-portion are along a first direction. The first element portion is electrically connected to the third element portion. The second element portion is electrically connected to the fourth element portion. The first element other-portion is electrically connected to the second element other-portion. The third element other-portion is electrically connected to the fourth element other-portion. The first conductive member includes a first conductive portion, a second conductive portion, and a first portion. A position of the first portion in a second direction is between a position of the first conductive portion in the second direction and a position of the second conductive portion in the second direction. The second direction crosses the first direction. The second conductive member includes a third conductive portion, a fourth conductive portion, and a second portion. A position of the second portion in the second direction is between a position of the third conductive portion in the second direction and a position of the fourth conductive portion in the second direction. The fourth magnetic element is between the second magnetic element and the first magnetic element in a third direction crossing a plane including the first and second directions. The third magnetic element is between the fourth magnetic element and the first magnetic element in the third direction. The second portion is between the second magnetic element and the fourth magnetic element in the third direction. The first portion is between the third magnetic element and the first magnetic element in the third direction. The fourth conductive portion is electrically connected to the second conductive portion. The first circuit is electrically connected to the first and third conductive portions. The first circuit is configured to supply a first current between the first conductive portion and the third conductive portion. The first current includes an alternating current component. The second circuit is electrically connected to a first connection point and a second connection point. The first connection point is between the first element portion and the third element portion. The second connection point is between the second element portion and the fourth element portion. The second circuit is configured to supply a second current between the first connection point and the second connection point.

According to one embodiment, an inspection device includes the magnetic sensor according to any one of the magnetic sensors described above, and a processor processing an output signal obtained from the magnetic sensor. The processor includes a first lock-in amplifier that receives input of the output signal and a signal corresponding to a frequency of the alternating current component included in the first current. The first lock-in amplifier is configured to output an output signal by using, as a reference wave, the signal corresponding to the frequency of the alternating current component included in the first current.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
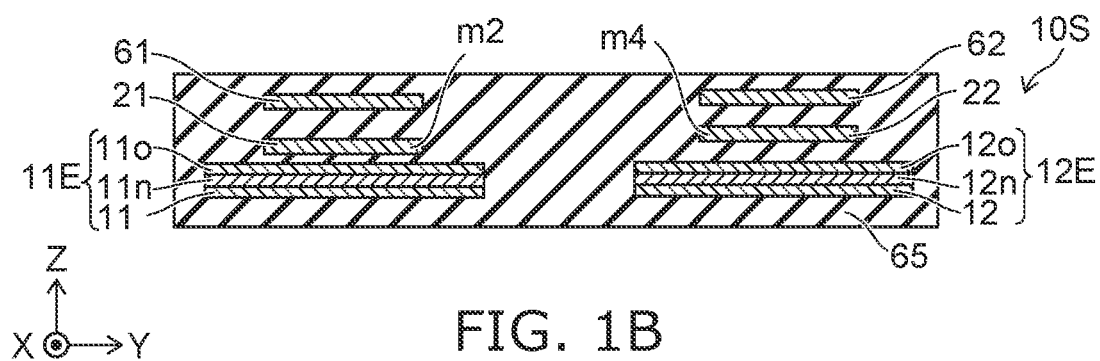
Figure 1C:
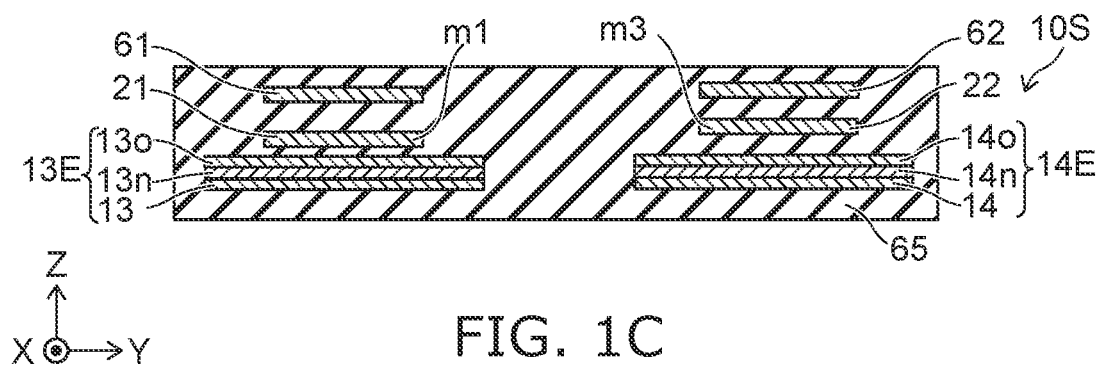
Figure 2A:
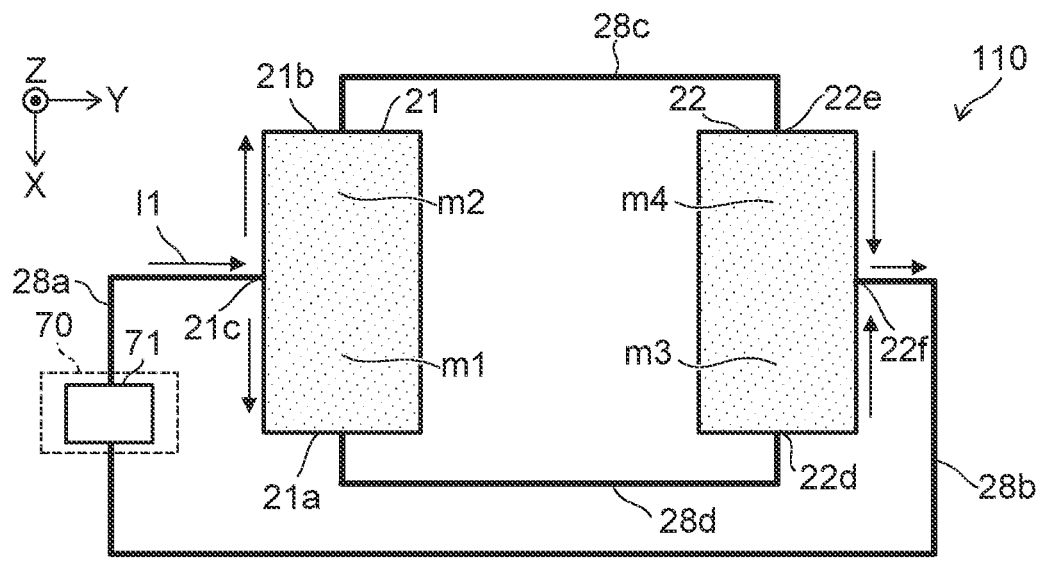
FIGS. 2A and 2B are schematic plan views illustrating the magnetic sensor according to the first embodiment.

FIGS. 1A to 1C are schematic views illustrating a magnetic sensor according to a first embodiment. FIG. 1A is a plan view illustrating a portion of the magnetic sensor. FIG. 1B is a line A1-A1 cross-sectional view of FIG. 1A. FIG. 1C is a line A2-A2 cross-sectional view of FIG. 1A. FIGS. 2A to 3 are schematic plan views illustrating the magnetic sensor according to the first embodiment.

In these drawings, some of the components are not illustrated as appropriate for easier viewing of the drawings.

As shown in FIGS. 1A to 2B, the magnetic sensor 110 according to the embodiment includes a sensor part 10S, a first circuit 71, and a second circuit 72. The sensor part 10S includes a magnetic element part 10P, a first conductive member 21, and a second conductive member 22. For example, the first circuit 71 and the second circuit 72 may be included in a circuit part 70.

As shown in FIG. 1A, the magnetic element part 10P includes a first magnetic element 11E, a second magnetic element 12E, a third magnetic element 13E, and a fourth magnetic element 14E. The first magnetic element 11E includes a first element portion 11e and a first element other-portion 11f. The second magnetic element 12E includes a second element portion 12e and a second element other-portion 12f. The third magnetic element 13E includes a third element portion 13e and a third element other-portion 13f. The fourth magnetic element 14E includes a fourth element portion 14e and a fourth element other-portion 14f. The first to fourth element portions 11e to 14e each may be, for example, one end portion. The first to fourth element other-portions 11f to 14f each may be, for example, one other end portion.

The first element other-portion 11f is between the first element portion 11e and the second element other-portion 12f in a first direction. The first direction is taken as a Y-axis direction. One direction perpendicular to the Y-axis direction is taken as an X-axis direction. A direction perpendicular to the Y-axis direction and the X-axis direction is taken as a Z-axis direction.

The second element portion 12e is between the first element other-portion 11f and the second element other-portion 12f in the first direction (the Y-axis direction). The third element other-portion 13f is between the third element portion 13e and the fourth element other-portion 14f in the first direction (the Y-axis direction). The fourth element portion 14e is between the third element other-portion 13f and the fourth element other-portion 14f in the first direction.

Figure 2B:
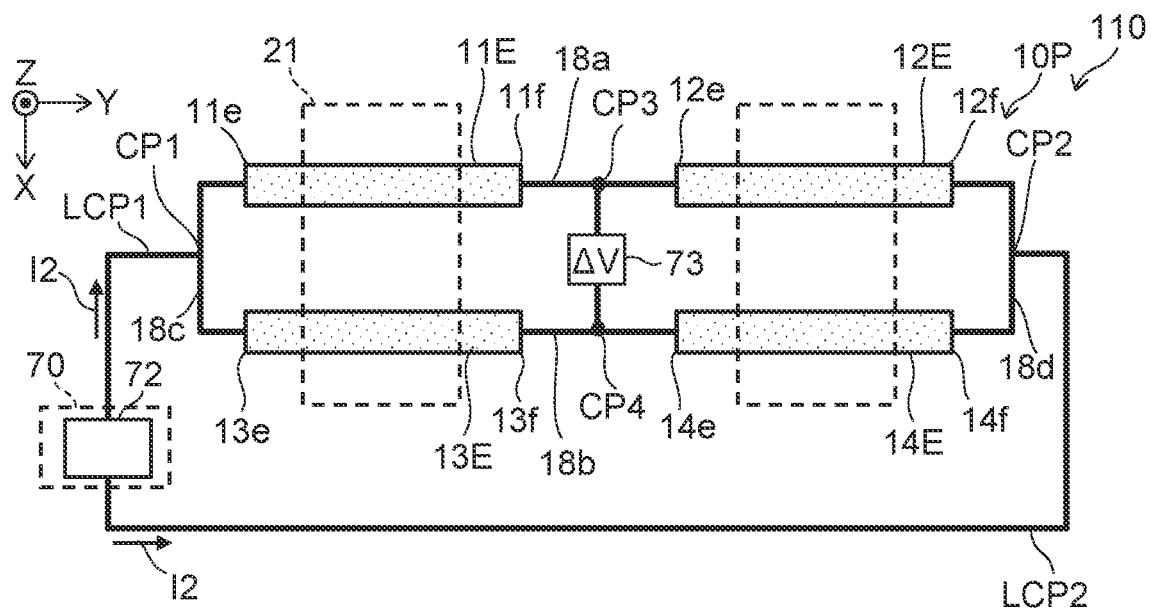
Figure 3:
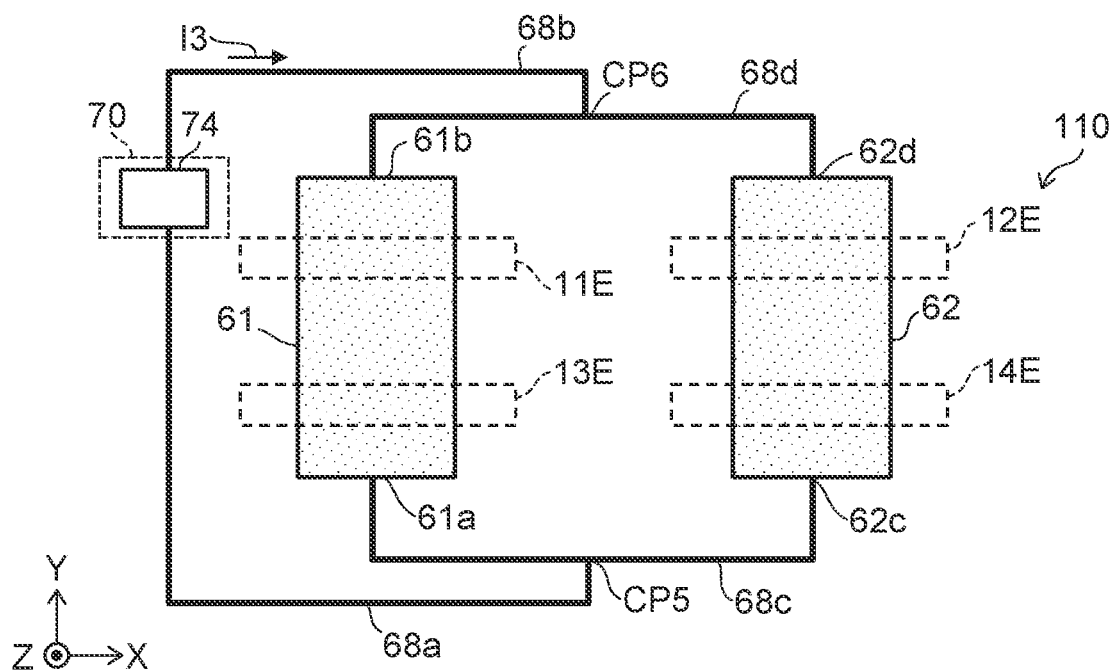
FIG. 3 is a schematic plan view illustrating the magnetic sensor according to the first embodiment.

As shown in FIG. 2B, the first element other-portion 11f is electrically connected to the second element portion 12e.

The third element other-portion 13f is electrically connected to the fourth element portion 14e. The first element portion 11e is electrically connected to the third element portion 13e. The second element other-portion 12f is electrically connected to the fourth element other-portion 14f. For example, these electrical connections may be performed by connection members 18a to 18d, etc.

As shown in FIGS. 1A and 2B, for example, the direction from the first magnetic element 11E toward the third magnetic element 13E is along a second direction (e.g., the X-axis direction). The direction from the second magnetic element 12E toward the fourth magnetic element 14E is along the second direction.

As shown in FIG. 2A, the first conductive member 21 includes a first conductive portion 21a, a second conductive portion 21b, a third conductive portion 21c, a first middle portion m1, and a second middle portion m2. The direction from the second conductive portion 21b toward the first conductive portion 21a is along the second direction that crosses the first direction. The second direction is, for example, the X-axis direction. The third conductive portion 21c is between the first conductive portion 21a and the second conductive portion 21b. The first middle portion m1 is between the first conductive portion 21a and the third conductive portion 21c. The second middle portion m2 is between the third conductive portion 21c and the second conductive portion 21b.

As shown in FIG. 1B, the direction from the first magnetic element 11E toward the second middle portion m2 is along a third direction. The third direction crosses a plane including the first and second directions. The third direction is, for example, the Z-axis direction. As shown in FIG. 1C, the direction from the third magnetic element 13E toward the first middle portion m1 is along the third direction (the Z-axis direction).

As shown in FIG. 2A, the second conductive member 22 includes a fourth conductive portion 22d, a fifth conductive portion 22e, a sixth conductive portion 22f, a third middle portion m3, and a fourth middle portion m4. The direction from the fifth conductive portion 22e toward the fourth conductive portion 22d is along the second direction (e.g., the X-axis direction). The sixth conductive portion 22f is between the fifth conductive portion 22e and the fourth conductive portion 22d. The third middle portion m3 is between the fourth conductive portion 22d and the sixth conductive portion 22f. The fourth middle portion m4 is between the sixth conductive portion 22f and the fifth conductive portion 22e.

As shown in FIG. 1B, the direction from the second magnetic element 12E toward the fourth middle portion m4 is along the third direction (the Z-axis direction). The direction from the fourth magnetic element 14E toward the third middle portion m3 is along the third direction.

As shown in FIG. 2A, the first conductive portion 21a is electrically connected to the fourth conductive portion 22d. The second conductive portion 21b is electrically connected to the fifth conductive portion 22e. For example, these electrical connections may be performed by connection members 28c and 28d, etc.

As shown in FIG. 2A, the first circuit 71 is electrically connected to the third and sixth conductive portions 21c and 22f. For example, the electrical connection may be performed by connection members 28a and 28b, etc. The first circuit 71 is configured to supply a first current I1 that includes an alternating current component between the third conductive portion 21c and the sixth conductive portion 22f. The first circuit 71 may be included in the circuit part 70.

As shown in FIG. 2B, the second circuit 72 is electrically connected to a first connection point CP1 and a second connection point CP2. The first connection point CP1 is the connection point between the first element portion 11e and the third element portion 13e. The second connection point CP2 is the connection point between the second element other-portion 12f and the fourth element other-portion 14f. The electrical connections may be performed by connection members LCP1 and LCP2, etc. The second circuit 72 is configured to supply a second current I2 between the first connection point CP1 and the second connection point CP2. For example, the second current I2 is a direct current. For example, the second current I2 may be supplied from a battery. The second circuit 72 may include a battery that has low noise.

The electrical resistances of the first to fourth magnetic elements 11E to 14E change according to the change of an external magnetic field. For example, the angle between the orientations of the magnetizations of the two magnetic layers included in each magnetic element changes according to the change of the external magnetic field. The electrical resistance changes according to the change of the angle. As shown in FIG. 2B, four magnetic elements have a bridge connection. For example, the effects of the noise, etc., are suppressed thereby. Detection is possible with higher accuracy.

When the first current I1 that includes the alternating current component is positive as shown in FIG. 2A, for example, a portion of the first current I1 flows through the first middle portion m1 in the orientation from the third conductive portion 21c toward the first conductive portion 21a. A portion of the first current I1 flows through the second middle portion m2 in the orientation from the third conductive portion 21c toward the second conductive portion 21b. A portion of the first current I1 flows through the third middle portion m3 in the orientation from the fourth conductive portion 22d toward the sixth conductive portion 22f. A portion of the first current I1 flows through the fourth middle portion m4 in the orientation from the fifth conductive portion 22e toward the sixth conductive portion 22f. When the first current I1 that includes the alternating current component is negative, the first current I1 flows in orientations that are the reverse of those described above.

The orientation (the phase) of the current magnetic field due to the current flowing through the first middle portion m1 is the reverse of the orientation (the phase) of the current magnetic field due to the current flowing through the second middle portion m2. The orientation (the phase) of the current magnetic field due to the current flowing through the third middle portion m3 is the reverse of the orientation (the phase) of the current magnetic field due to the current flowing through the fourth middle portion m4. The orientation (the phase) of the current magnetic field due to the current flowing through the first middle portion m1 is the reverse of the orientation (the phase) of the current magnetic field due to the current flowing through the third middle portion m3. The orientation (the phase) of the current magnetic field due to the current flowing through the second middle portion m2 is the reverse of the orientation (the phase) of the current magnetic field due to the current flowing through the fourth middle portion m4.

The current magnetic field from the first middle portion m1 is applied to the third magnetic element 13E. The current magnetic field from the second middle portion m2 is applied to the first magnetic element 11E. The current magnetic field from the third middle portion m3 is applied to the fourth magnetic element 14E. The current magnetic field from the fourth middle portion m4 is applied to the second magnetic element 12E.

As described below, detection is possible with higher sensitivity because the current magnetic field that is due to the first current I1 including the alternating current component is applied to the magnetic elements in addition to the external magnetic field of the detection object.

As shown in FIG. 1B, for example, the first magnetic element 11E includes a first magnetic layer 11, a first counter magnetic layer 11o, and a first nonmagnetic layer 11n provided between the first magnetic layer 11 and the first counter magnetic layer 11o. The direction from the first magnetic layer 11 toward the first counter magnetic layer 11o is along the third direction (e.g., the Z-axis direction).

As shown in FIG. 1B, for example, the second magnetic element 12E includes a second magnetic layer 12, a second counter magnetic layer 12o, and a second nonmagnetic layer 12n provided between the second magnetic layer 12 and the second counter magnetic layer 12o. The direction from the second magnetic layer 12 toward the second counter magnetic layer 12o is along the third direction (e.g., the Z-axis direction).

As shown in FIG. 1C, for example, the third magnetic element 13E includes a third magnetic layer 13, a third counter magnetic layer 13o, and a third nonmagnetic layer 13n provided between the third magnetic layer 13 and the third counter magnetic layer 13o. The direction from the third magnetic layer 13 toward the third counter magnetic layer 13o is along the third direction (e.g., the Z-axis direction).

As shown in FIG. 1C, for example, the fourth magnetic element 14E includes a fourth magnetic layer 14, a fourth counter magnetic layer 14o, and a fourth nonmagnetic layer 14n provided between the fourth magnetic layer 14 and the fourth counter magnetic layer 14o. The direction from the fourth magnetic layer 14 toward the fourth counter magnetic layer 14o is along the third direction (e.g., the Z-axis direction). The first to fourth magnetic elements 11E to 14E are, for example, GMRs (Giant Magneto Resistive effect) elements.

For example, both the orientation of the magnetization of the first magnetic layer 11 and the orientation of the magnetization of the first counter magnetic layer 11o may change with respect to the external magnetic field. For example, the first to fourth magnetic layers 11 to 14 and the first to fourth counter magnetic layers 11o to 14o are free magnetic layers. For example, the configuration of a double free layer is applicable to the first to fourth magnetic elements 11E to 14E. In such a case, the orientations of the magnetizations of the two magnetic layers included in one magnetic element change. The change of the angle between the two magnetizations is large. A larger change of the electrical resistance is obtained thereby. For example, high sensitivity is obtained.

According to the embodiment, the minimum detectable magnetic field strength is, for example, not less than 100 pT. There are also cases where the minimum detectable magnetic field strength is, for example, not less than 10 pT.

For example, in the state in which there is no external magnetic field, the antiparallel magnetic alignment of the two magnetic layers is stabilized in the X-axis direction. For example, the change of the electrical resistance of the magnetic element with respect to the external magnetic field easily has a good even function.

An example of the change of the electrical resistance of the magnetic element will now be described. One magnetic element (the first magnetic element 11E) will be described.

Figure 4:
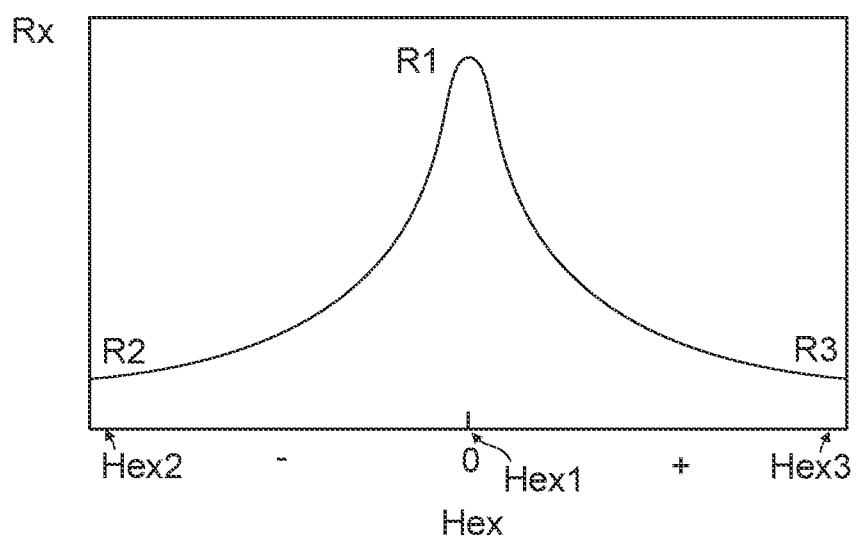
FIG. 4 is a graph illustrating a characteristic of the magnetic sensor according to the first embodiment.

FIG. 4 is a graph illustrating a characteristic of the magnetic sensor according to the first embodiment.

The horizontal axis of FIG. 4 is the intensity of an external magnetic field Hex applied to the first magnetic element 11E. The vertical axis is an electrical resistance Rx of the first magnetic element 11E. FIG. 4 corresponds to the R-H characteristic.

As shown in FIG. 4, the electrical resistance Rx has an even-function characteristic of a magnetic field (the external magnetic field Hex, e.g., a magnetic field in the X-axis direction) applied to the first magnetic element 11E. For example, the electrical resistance Rx has a first value R1 when a first magnetic field Hex1 is applied to the first magnetic element 11E. The electrical resistance Rx has a second value R2 when a second magnetic field Hex2 is applied to the first magnetic element 11E. The electrical resistance Rx has a third value R3 when a third magnetic field Hex3 is applied to the first magnetic element 11E. The absolute value of the first magnetic field Hex1 is less than the absolute value of the second magnetic field Hex2 and less than the absolute value of the third magnetic field Hex3. For example, the first magnetic field Hex1 is substantially 0. The orientation of the second magnetic field Hex2 is the reverse of the orientation of the third magnetic field Hex3. The first value R1 is less than the second value R2 and less than the third value R3.

An example in which the first current I1 is an alternating current and substantially does not include a direct current component will now be described. The first current I1. (the alternating current) is supplied to the first conductive member 21; and the alternating current magnetic field that is due to the alternating current is applied to the first magnetic element 11E. An example of the change of the electrical resistance Rx at this time will now be described.

Figure 5A:
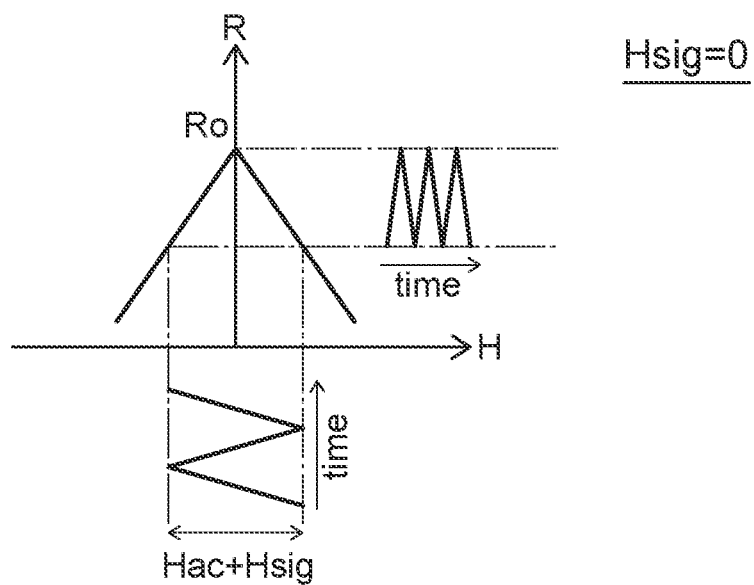
FIGS. 5A to 5C are graphs illustrating characteristics of the magnetic sensor according to the first embodiment.
Figure 5B:
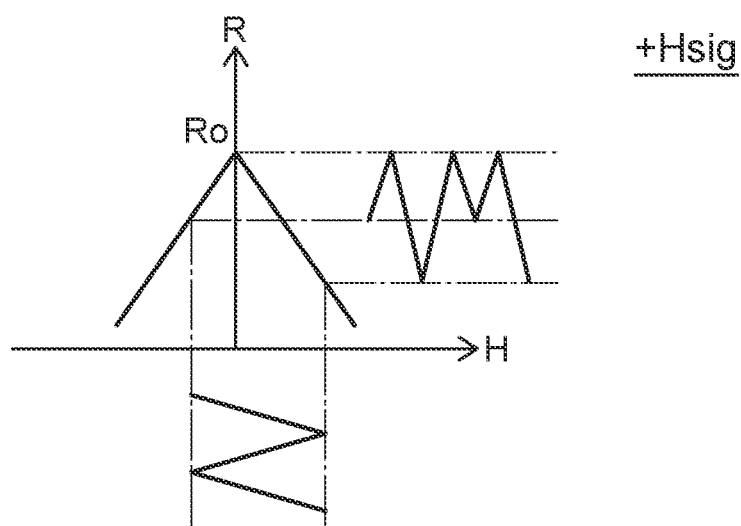
Figure 5C:
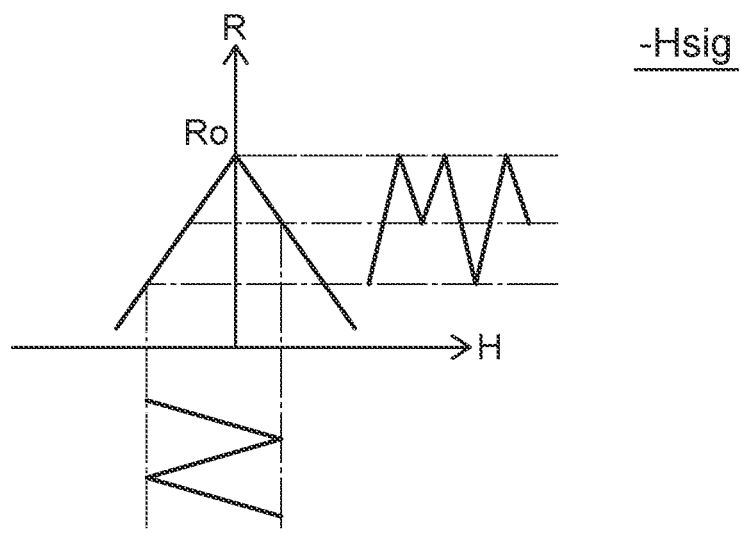

FIGS. 5A to 5C are graphs illustrating characteristics of the magnetic sensor according to the first embodiment.

FIG. 5A shows characteristics when a signal magnetic field Hsig (the external magnetic field) applied to the first magnetic element 11E is 0. FIG. 5B shows characteristics when the signal magnetic field Hsig is positive. FIG. 5C shows characteristics when the signal magnetic field Hsig is negative. These figures show the relationship between a magnetic field H and a resistance R (corresponding to the electrical resistance Rx).

As shown in FIG. 5A, when the signal magnetic field Hsig is 0, the resistance R has a characteristic that is symmetric with respect to the positive and negative magnetic field H. When an alternating current magnetic field Hac is zero, the resistance R is a resistance Ro. For example, a substantially symmetric resistance change characteristic is obtained. The fluctuation of the resistance R with respect to the alternating current magnetic field Hac has substantially the same value between the positive and negative polarities. The period of the change of the resistance R is 2 times the period of the alternating current magnetic field Hac. The change of the resistance R substantially does not include the frequency component of the alternating current magnetic field Hac.

As shown in FIG. 5B, the characteristic of the resistance R shifts to the positive magnetic field H side when a positive signal magnetic field Hsig is applied. The resistance R becomes low for the alternating current magnetic field Hac on the positive side. The resistance R becomes high for the alternating current magnetic field Hac on the negative side.

As shown in FIG. 5C, the characteristic of the resistance R shifts to the negative magnetic field H side when a negative signal magnetic field Hsig is applied. The resistance R becomes high for the alternating current magnetic field Hac on the positive side. The resistance R becomes low for the alternating current magnetic field Hac on the negative side.

Resistances R having mutually-different fluctuation occur for the positive and negative of the alternating current magnetic field Hac when a signal magnetic field Hsig of a prescribed magnitude is applied. The period of the fluctuation of the resistance R with respect to the positive and negative alternating current magnetic field Hac is equal to the period of the alternating current magnetic field Hac. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating current magnetic field Hac is taken as an alternating current frequency fac. In such a case, an output that corresponds to the signal magnetic field Hsig at frequencies of fac±fsig is generated.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, there is an application in which the magnetic field generated from a living body is detected using the magnetic sensor 110. When detecting such a biological magnetic field (e.g., neuromagnetism, cardiomagnetism, a neuron, etc.), the signal frequency fsig is not more than 1 kHz. In such a case, the alternating current frequency fac is, for example, not less than 100 kHz.

For example, operating characteristics similar to those of the first magnetic element 11E described above are obtained for the second to fourth magnetic elements 12E to 14E as well. In the magnetic sensor 110 according to the embodiment, the external magnetic field Hex (the signal magnetic field Hsig) that is the detection object can be detected with high sensitivity by using such characteristics. Higher sensitivity is obtained by the first to fourth magnetic elements 11E to 14E having a bridge connection.

According to the embodiment, the first to fourth magnetic elements 11E to 14E, the first conductive member 21, and the second conductive member 22 such as those described above are combined. The alternating current magnetic fields that are generated by the first current I1 flowing in the first and second conductive members 21 and 22 are applied to the first to fourth magnetic elements 11E to 14E. The phases of the alternating current magnetic fields applied to the magnetic elements have reverse phases. For example, a noise component that has a period that is 2 times the period of the alternating current component of the first current I1 can be suppressed.

As shown in FIG. 2B, the magnetic sensor 110 may further include a third circuit 73. The third circuit 73 is electrically connected to a third connection point CP3 and a fourth connection point CP4. The third connection point CP3 is a connection point between the first element other-portion 11f and the second element portion 12e. The fourth connection point CP4 is a connection point between the third element other-portion 13f and the fourth element portion 14e. The third circuit 73 is configured to detect a change ΔV of the potential between the third connection point CP3 and the fourth connection point CP4. The external magnetic field can be detected with higher sensitivity by the third circuit 73 detecting the change ΔV of the potential between the two midpoints of the bridge circuit. For example, by detecting a component in a portion of the frequency range of the change ΔV of the potential between the midpoints, the noise can be reduced, and the external magnetic field can be detected with higher sensitivity. The detected frequency range includes, for example, a frequency range that has the frequency range of the alternating current component of the first current I1 as a center and is enlarged to the frequency range of the signal magnetic field. For example, the third circuit 73 may be included in the circuit part 70. The third circuit 73 may include a lock-in amplifier that uses the alternating current frequency supplied from the first circuit 71 as a reference signal.

As shown in FIGS. 1B, 1C, and 3, the magnetic sensor 110 may include a first conductive layer 61, a second conductive layer 62, and a fourth circuit 74.

As shown in FIGS. 1B and 1C, the first conductive layer 61 overlaps the first and third magnetic elements 11E and 13E in the third direction (e.g., the Z-axis direction). The second conductive layer 62 overlaps the second and fourth magnetic elements 12E and 14E in the third direction.

As shown in FIG. 3, the first conductive layer 61 includes a first conductive layer end portion 61a and a second conductive layer end portion 61b. The orientation from the second conductive layer end portion 61b toward the first conductive layer end portion 61a is along the second direction (e.g., the X-axis direction). The second conductive layer 62 includes a third conductive layer end portion 62c and a fourth conductive layer end portion 62d. The orientation from the fourth conductive layer end portion 62d toward the third conductive layer end portion 62c is along the second direction. The first conductive layer end portion 61a is electrically connected to the third conductive layer end portion 62c. The second conductive layer end portion 61b is electrically connected to the fourth conductive layer end portion 62d. These electrical connections are performed by connection members 68c and 68d, etc.

The fourth circuit 74 is electrically connected to a fifth connection point CP5 and a sixth connection point CP6. The fifth connection point CP5 is a connection point between the first conductive layer end portion 61a and the third conductive layer end portion 62c. The sixth connection point CP6 is a connection point between the second conductive layer end portion 61b and the fourth conductive layer end portion 62d. For example, the electrical connections are performed by connection members 68a and 68d, etc. The fourth circuit 74 is configured to supply a third current I3 between the fifth connection point CP5 and the sixth connection point CP6. For example, the effects of noise existing externally (e.g., the effects of geomagnetism, etc.) can be suppressed by the third current I3 due to the fourth circuit 74. Higher sensitivity is easily obtained.

As shown in FIG. 1C, for example, the first middle portion m1 is between the third magnetic element 13E and a portion of the first conductive layer 61. As shown in FIG. 1B, the second middle portion m2 is between the first magnetic element 11E and another portion of the first conductive layer 61. As shown in FIG. 1C, the third middle portion m3 is between the fourth magnetic element 14E and a portion of the second conductive layer 62. As shown in FIG. 1B, the fourth middle portion m4 is between the second magnetic element 12E and another portion of the second conductive layer 62.

As shown in FIGS. 1B and 1C, an insulating member 65 may be provided around the first to fourth magnetic elements 11E to 14E, the first conductive member 21, the second conductive member 22, the first conductive layer 61, and the second conductive layer 62.

In one example of the magnetic sensor 110, in the state in which there is no external magnetic field, the value of the second current I2 is set so that the orientations of the magnetization of the first magnetic layer 11 and the magnetization of the first counter magnetic layer 110 have an antiparallel alignment in the ±X-directions. The direction of the second current I2 is along the Y-axis direction. The magnetic field that is generated by the second current I2 has mutually-reverse directions with respect to the two magnetic layers. The magnetizations of the two magnetic layers are aligned in the ±X-directions. The orientations of the magnetic fields of the two magnetic layers are changed toward the Y-axis direction by applying an external magnetic field including a Y-axis direction component to the magnetic element. The angle between the magnetizations of the two magnetic layers is reduced. The change amount of the angle between the two magnetizations corresponding to the change of the external magnetic field is 2 times the change amount of the angle when the orientation of the magnetization of one magnetic layer changes. In the magnetic sensor 110, the change of the electrical resistance is large.

As shown in FIG. 1A, the first magnetic element 11E has a first length L1 along the first direction (the Y-axis direction), and a first cross length W1 along the second direction (e.g., the X-axis direction). The first length L1 is greater than the first cross length W1. The second magnetic element 12E has a second length L2 along the first direction, and a second cross length W2 along the second direction. The second length L2 is greater than the second cross length W2. The third magnetic element 13E has a third length L3 along the first direction, and a third cross length W3 along the second direction. The third length L3 is greater than the third cross length W3. The fourth magnetic element 14E has a fourth length L4 along the first direction, and a fourth cross length W4 along the second direction. The fourth length L4 is greater than the fourth cross length W4. The magnetizations of the magnetic layers are favorably controlled.

In such a configuration, for example, in the state in which there is no external magnetic field, for example, the magnetizations of the two magnetic layers included in the magnetic element can be stabilized in the ±X-directions by the magnetic field generated by the second current I2. For example, it is difficult to align the orientations of the magnetic layer magnetizations if the first length L1 is less than the first cross length W1. According to the embodiment, for example, higher sensitivity is obtained by changing both of the orientations of the magnetizations of the two magnetic layers.

For example, the change amount of the angle between the two magnetizations corresponding to the change of the external magnetic field is 2 times the change amount of the angle when only the orientation of the magnetization of one magnetic layer changes. The change of the electrical resistance can be large.

According to the embodiment, for example, the first length L1 is not less than 20 μm and not more than 200 μm. The first cross length W1 is, for example, not less than 5 μm and not more than 20 μm. Thereby, the orientation of the magnetization of the magnetic layer is changed (e.g., rotated) with a small hysteresis and with high sensitivity. For example, the thickness (the length along the Z-axis direction) of the first magnetic layer 11 is not less than 0.8 times and not more than 1.2 times the thickness (the length along the Z-axis direction) of the first counter magnetic layer 11o. For example, a good even-function characteristic is easily obtained thereby.

According to the embodiment, a magnetic bias magnetic substance such as IrMn or the like is not provided in the first to fourth magnetic elements 11E to 14E. For example, the thickness of the first magnetic layer 11 is not less than 0.8 times and not more than 1.2 times the thickness of the first counter magnetic layer 11o. The former may be not less than 0.9 times and not more than 1.1 times the latter. Such thicknesses are applicable to the second to fourth magnetic elements 12E to 14E as well. The thicknesses of the magnetic layers included in the first to fourth magnetic elements 11E to 14E are, for example, not less than 2 nm and not more than 10 nm. By such a configuration, the characteristics of the first to fourth magnetic elements 11E to 14E are easily and appropriately controlled. For example, a good even-function characteristic is easily obtained. For example, the magnetizations of these magnetic layers are easily and appropriately controlled. For example, the magnetizations of the two magnetic layers included in the magnetic element are easily rotated to be the same.

For example, the first magnetic layer 11 and the first counter magnetic layer 11o include at least one of CoFe or NiFe. For example, the first nonmagnetic layer 11n includes Cu. The thickness (the length along the Z-axis direction) of the first nonmagnetic layer 11n is about 2 nm (e.g., not less than 1.6 nm and not more than 2.4 nm). In such a case, the magnetizations of the two magnetic layers are antiparallel. For example, the magnetizations of the two magnetic layers easily become antiparallel due to a small second current I2.

For example, noise is easily generated when the magnetization of one of the two magnetic layers is fixed and the magnetization of the other of the two magnetic layers changes. It is considered that this is because the even-function characteristic easily degrades due to a slight disturbance of the fixation direction of the magnetization in this structure. In the configuration in which the orientations of the magnetizations of the two magnetic layers change, a stable even-function characteristic when there is no external magnetic field is easily obtained by the second current I2.

Figure 6:
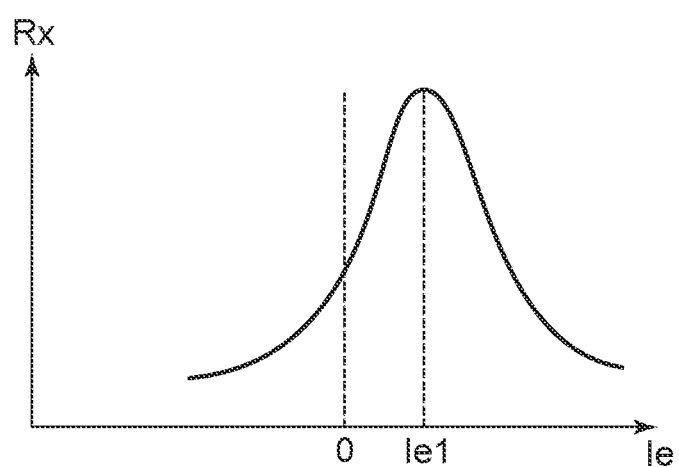
FIG. 6 is a graph illustrating a characteristic of the magnetic sensor according to the first embodiment.

FIG. 6 is a graph illustrating a characteristic of the magnetic sensor according to the first embodiment.

The horizontal axis of FIG. 6 is a current Ie supplied to the magnetic element (e.g., the first magnetic element 11E). The vertical axis is the electrical resistance Rx of the magnetic element (e.g., the first magnetic element 11E). FIG. 6 illustrates the characteristic in a state in which the external magnetic field Hex (the signal magnetic field Hsig) that is the detection object is not applied to the magnetic element (in the example, the magnetic sensor 110). As shown in FIG. 6, the electrical resistance Rx of the first magnetic element 11E has a peak when the current Ie supplied to the first magnetic element 11E has a first current value Ie1. As shown in FIG. 6, the first current value Ie1 at which the electrical resistance Rx has a peak is not 0. It is considered that this is due to the effects of noise (e.g., the effects of geomagnetism, etc.) that exists externally and is applied to the magnetic element (in the example, the magnetic sensor 110). According to the embodiment, the second circuit 72 sets the magnitude of the second current I2 to the magnitude of the first current value Ic1. The effects of the noise existing externally are suppressed thereby, and a good even-function characteristic is obtained.

Second Embodiment

Figure 7A:
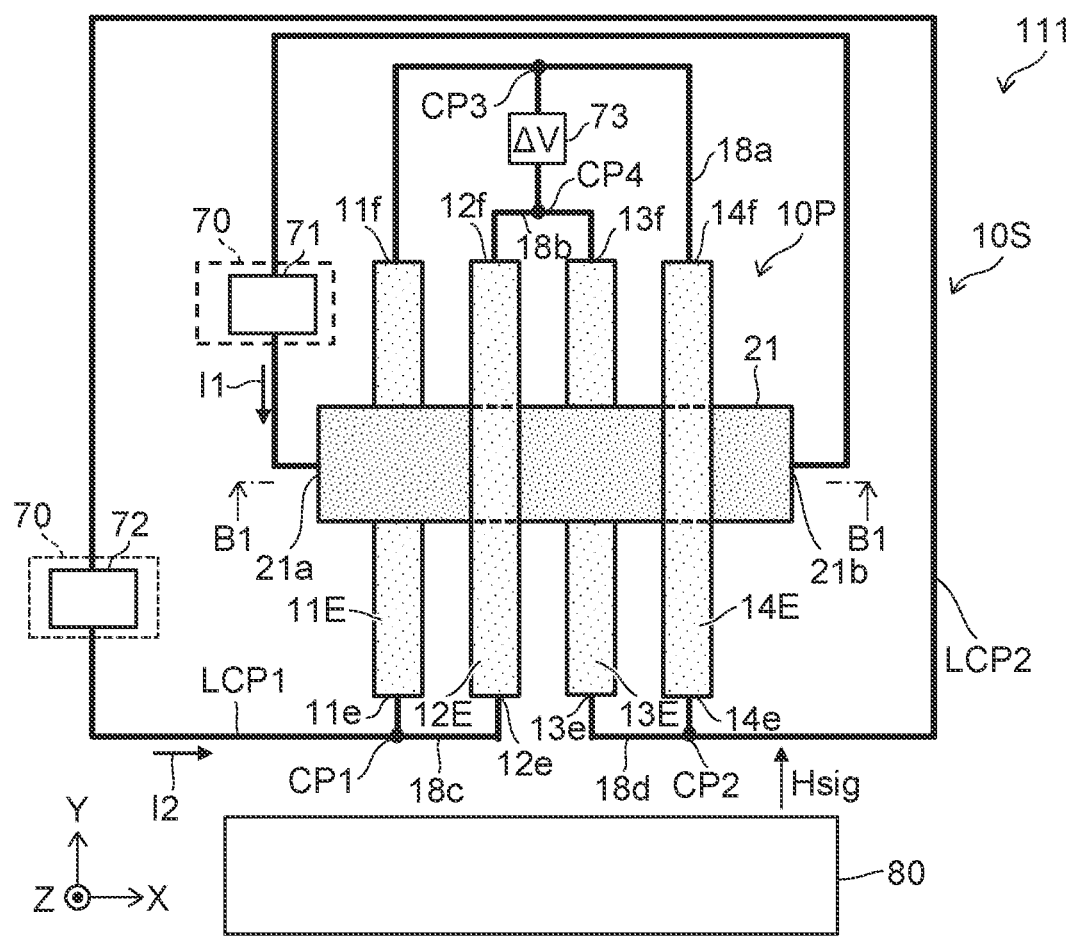
FIGS. 7A and 7B are schematic views illustrating a magnetic sensor according to a second embodiment.
Figure 7B:
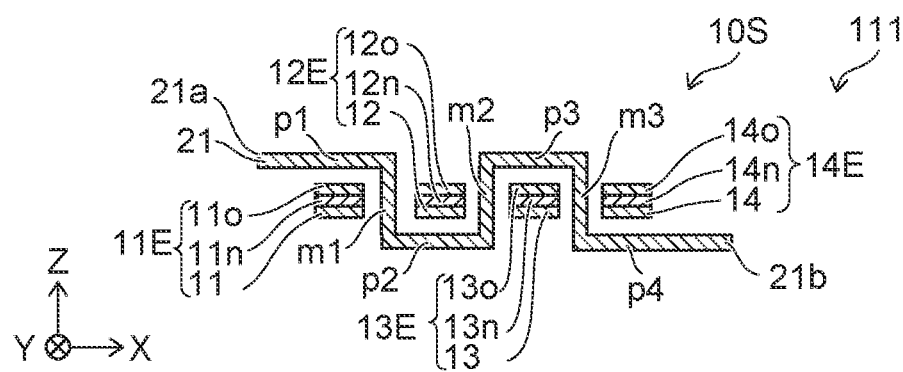

FIGS. 7A and 7B are schematic views illustrating a magnetic sensor according to a second embodiment.

FIG. 7A is a plan view illustrating a portion of the magnetic sensor. FIG. 7B is a line B1-B1 cross-sectional view of FIG. 7A.

As shown in FIG. 7A, the magnetic sensor 111 according to the embodiment includes the sensor part 10S, the first circuit 71, and the second circuit 72. The sensor part 10S includes the magnetic element part 10P and the first conductive member 21.

The magnetic element part 10P includes the first magnetic element 11E, the second magnetic element 12E, the third magnetic element 13E, and the fourth magnetic element 14E. The first magnetic element 11E includes the first element portion 11e and the first element other-portion 11f. The second magnetic element 12E includes the second element portion 12e and the second element other-portion 12f. The third magnetic element 13E includes the third element portion 13e and the third element other-portion 13f. The fourth magnetic element 14E includes the fourth element portion 14e and the fourth element other-portion 14f.

The direction from the first element portion 11e toward the first element other-portion 11f, the direction from the second element portion 12e toward the second element other-portion 12f, the direction from the third element portion 13e toward the third element other-portion 13f, and the direction from the fourth element portion 14e toward the fourth element other-portion 14f are along the first direction (e.g., the Y-axis direction).

The first element portion 11e is electrically connected to the second element portion 12e. The third element portion 13e is electrically connected to the fourth element portion 14e. The first element other-portion 11f is electrically connected to the fourth element other-portion 14f. The second element other-portion 12f is electrically connected to the third element other-portion 13f. For example, these electrical connections are performed by the connection members 18a to 18d, etc.

As shown in FIGS. 7A and 7B, the first conductive member 21 includes the first conductive portion 21a, the second conductive portion 21b, a first portion p1, a second portion p2, a third portion p3, and a fourth portion p4.

The position in the second direction of the first portion p1 is between the position in the second direction of the first conductive portion 21a and the position in the second direction of the second conductive portion 21b. The second direction crosses the first direction. The second direction is, for example, the X-axis direction.

The position in the second direction of the second portion p2 is between the position in the second direction of the first portion p1 and the position in the second direction of the second conductive portion 21b. The position in the second direction of the third portion p3 is between the position in the second direction of the second portion p2 and the position in the second direction of the second conductive portion 21b. The position in the second direction of the fourth portion p4 is between the position in the second direction of the third portion p3 and the position in the second direction of the second conductive portion 21b.

As shown in FIG. 7B, a first orientation from the first magnetic element 11E toward the first portion p1 is along the third direction. The third direction crosses a plane including the first and second directions. The third direction is, for example, the Z-axis direction. A second orientation from the second magnetic element 12E toward the second portion p2 is the reverse of the first orientation recited above. A third orientation from the third magnetic element 13E toward the third portion p3 is the same as the first orientation recited above. A fourth orientation from the fourth magnetic element 14E toward the fourth portion p4 is the reverse of the first orientation recited above.

The first circuit 71 is electrically connected to the first and second conductive portions 21a and 21b. The first circuit 71 is configured to supply the first current I1 including the alternating current component between the first conductive portion 21a and the second conductive portion 21b.

The second circuit 72 is electrically connected to the first connection point CP1 that is between the first element portion 11e and the second element portion 12e, and to the second connection point CP2 that is between the third element portion 13e and the fourth element portion 14e. The second circuit 72 is configured to supply the second current I2 between the first connection point CP1 and the second connection point CP2.

A portion of the second current I2 flows through the first magnetic element 11E in the orientation from the first element portion 11e toward the first element other-portion 11f. A portion of the second current I2 flows through the second magnetic element 12E in the orientation from the second element portion 12e toward the second element other-portion 12f. A portion of the second current I2 flows through the third magnetic element 13E in the orientation from the third element other-portion 13f toward the third element portion 13e. A portion of the second current I2 flows through the fourth magnetic element 14E in the orientation from the fourth element other-portion 14f toward the fourth element portion 14e.

As shown in FIG. 7B, the vertical relationship of the first magnetic element 11E with respect to the first conductive member 21 is the reverse of the vertical relationship of the second magnetic element 12E with respect to the first conductive member 21. The vertical relationship of the third magnetic element 13E with respect to the first conductive member 21 is the reverse of the vertical relationship of the fourth magnetic element 14E with respect to the first conductive member 21. The effects of the current magnetic field due to the first conductive member 21 are suppressed by the bridge connection of four such magnetic elements. Higher sensitivity is obtained.

For example, the magnetic sensor 111 may further include the third circuit 73. The third circuit 73 is electrically connected to the third connection point CP3 that is between the first element other-portion 11f and the fourth element other-portion 14f, and to the fourth connection point CP4 that is between the second element other-portion 12f and the third element other-portion 13f. The third circuit 73 is configured to detect the change ΔV of the potential between the third connection point CP3 and the fourth connection point CP4.

As shown in FIG. 7A, the signal magnetic field Hsig (the external magnetic field) from a detection object 80 is detected by the magnetic sensor 111. The detection object 80 may be, for example, an electrical circuit, etc. The detection object 80 can be inspected by the magnetic sensor 111 detecting the signal magnetic field Hsig that is based on the currents flowing through the conductive members (e.g., wiring, etc.) included in the electrical circuit.

As shown in FIG. 7B, the first conductive member 21 may further include the first middle portion m1, the second middle portion m2, and the third middle portion m3. The first middle portion m1 is between the first magnetic element 11E and the second magnetic element 12E in the second direction (e.g., the X-axis direction). The second middle portion m2 is between the second magnetic element 12E and the third magnetic element 13E in the second direction. The third middle portion m3 is between the third magnetic element 13E and the fourth magnetic element 14E in the second direction. The first conductive portion 21a, the second conductive portion 21b, the first portion p1, the second portion p2, the third portion p3, the fourth portion p4, the first middle portion m1, the second middle portion m2, and the third middle portion m3 are continuous with each other.

In the magnetic sensor 111 as shown in FIG. 7B, the four magnetic elements are arranged in the X-axis direction. The second magnetic element 12E is between the first magnetic element 11E and the fourth magnetic element 14E in the second direction (e.g., the X-axis direction). The third magnetic element 13E is between the second magnetic element 12E and the fourth magnetic element 14E in the second direction.

Figure 8:
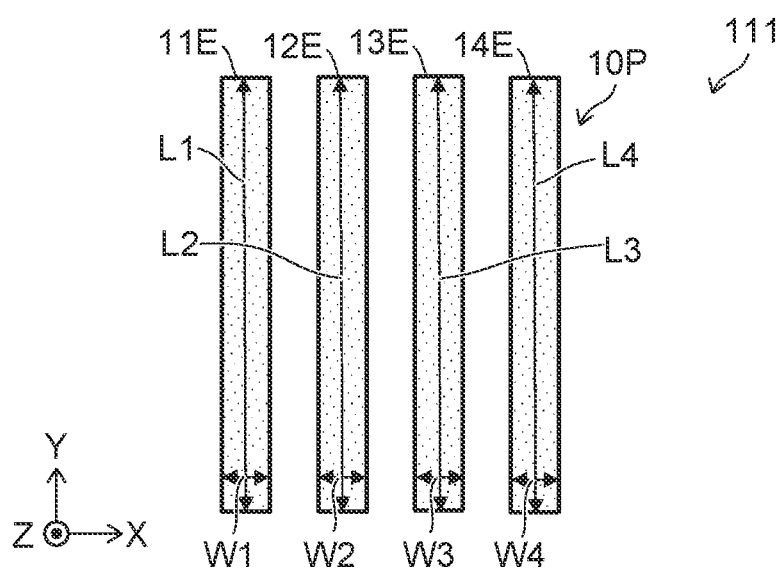
FIG. 8 is a schematic plan view illustrating a portion of the magnetic sensor according to the second embodiment.

FIG. 8 is a schematic plan view illustrating a portion of the magnetic sensor according to the second embodiment.

FIG. 8 illustrates the shapes of the first to fourth magnetic elements 11E to 14E.

As shown in FIG. 8, the first magnetic element 11E has the first length L1 that is along the first direction (the Y-axis direction), and the first cross length W1 that is along the second direction (e.g., the X-axis direction). The first length L1 is greater than the first cross length W1. The second magnetic element 12E has the second length L2 that is along the first direction, and the second cross length W2 that is along the second direction. The second length L2 is greater than the second cross length W2. The third magnetic element 13E has the third length L3 that is along the first direction, and the third cross length W3 that is along the second direction. The third length L3 is greater than the third cross length W3. The fourth magnetic element 14E has the fourth length L4 that is along the first direction, and the fourth cross length W4 that is along the second direction. The fourth length L4 is greater than the fourth cross length W4. For example, higher sensitivity is obtained by changing both of the orientations of the magnetizations of the two magnetic layers having such a shape. For example, the magnetizations of the two magnetic layers included in the magnetic element in the state in which there is no external magnetic field are easily stabilized in the ±X-directions by the magnetic field generated by the second current I2.

Third Embodiment

Figure 9A:
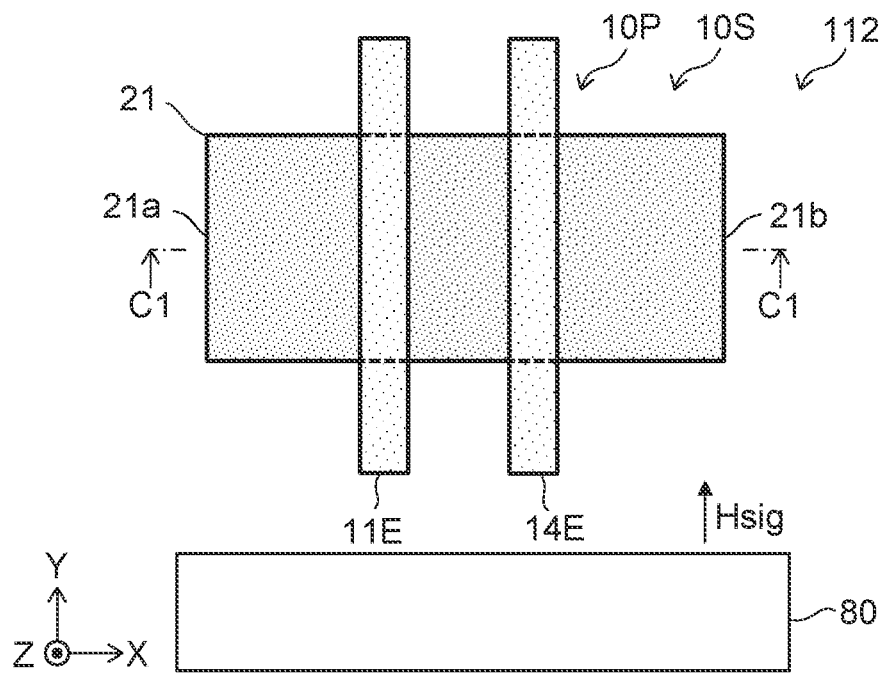
FIGS. 9A and 9B are schematic views illustrating a magnetic sensor according to a third embodiment.
Figure 9B:
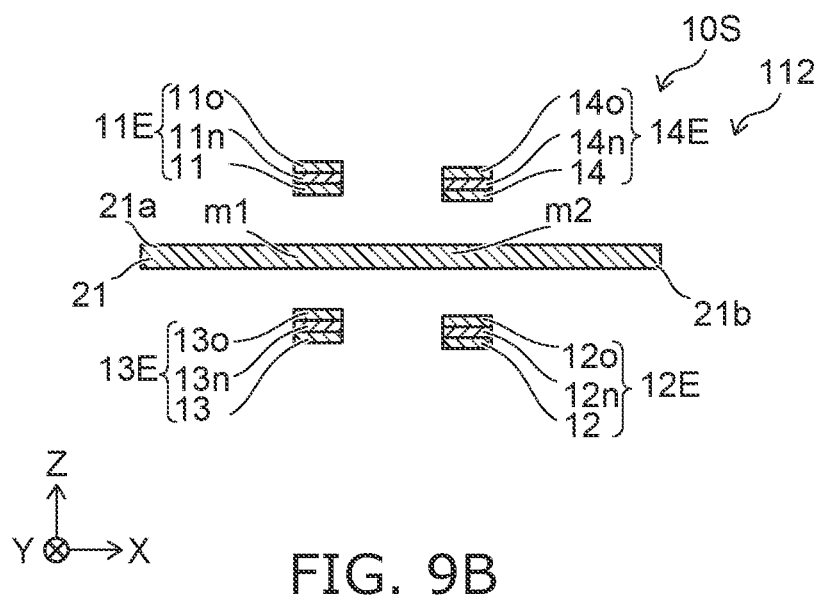

FIGS. 9A and 9B are schematic views illustrating a magnetic sensor according to a third embodiment.

FIG. 9A is a plan view illustrating a portion of the magnetic sensor. FIG. 9B is a line C1-C1 cross-sectional view of FIG. 9A.

Figure 10A:
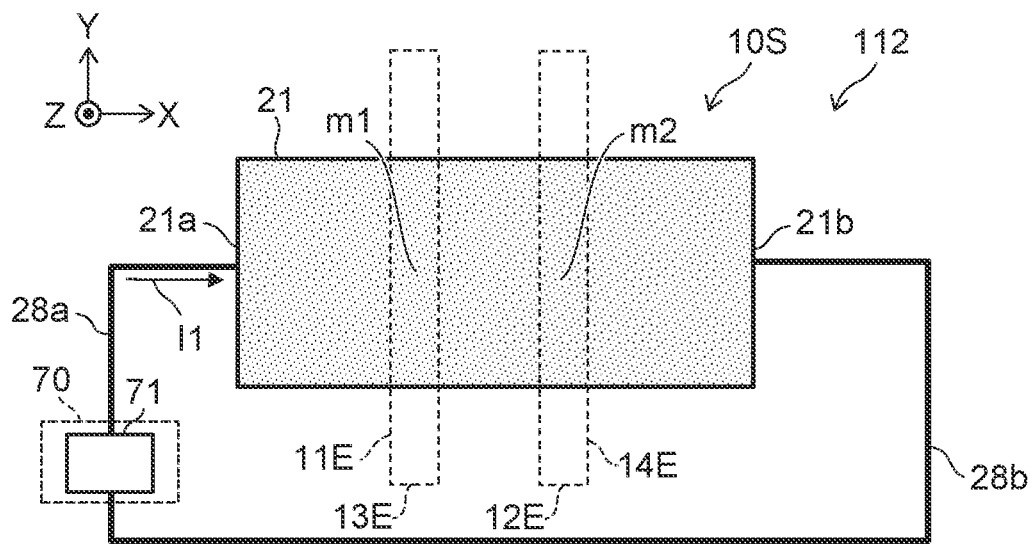
FIGS. 10A and 10B are schematic plan views illustrating the magnetic sensor according to the third embodiment.
Figure 10B:
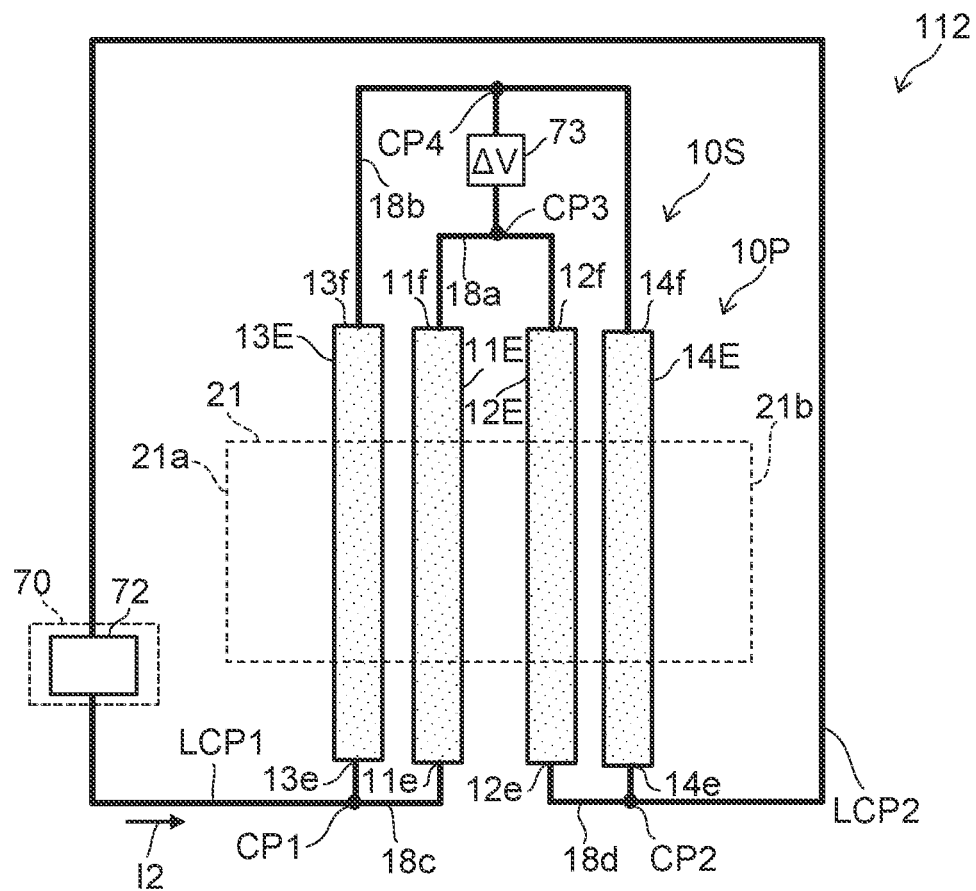

FIGS. 10A and 10B are schematic plan views illustrating the magnetic sensor according to the third embodiment.

As shown in FIGS. 9A, 10A, and 10B, the magnetic sensor 112 according to the embodiment includes the sensor part 10S, the first circuit 71, and the second circuit 72. The sensor part 10S includes the magnetic element part 10P and the first conductive member 21.

The magnetic element part 10P includes the first magnetic element 11E, the second magnetic element 12E, the third magnetic element 13E, and the fourth magnetic element 14E.

The first magnetic element 11E includes the first element portion 11e and the first element other-portion 11f. The second magnetic element 12E includes the second element portion 12e and the second element other-portion 12f. The third magnetic element 13E includes the third element portion 13e and the third element other-portion 13f. The fourth magnetic element 14E includes the fourth element portion 14e and the fourth element other-portion 14f.

The direction from the first element portion 11e toward the first element other-portion 11f, the direction from the second element portion 12e toward the second element other-portion 12f, the direction from the third element portion 13e toward the third element other-portion 13f, and the direction from the fourth element portion 14e toward the fourth element other-portion 14f are along the first direction (e.g., the Y-axis direction).

As shown in FIG. 9B, the second direction from the first magnetic element 11E toward the fourth magnetic element 14E crosses the first direction. The second direction is, for example, the X-axis direction. The direction from the third magnetic element 13E toward the second magnetic element 12E is along the second direction. The direction from the third magnetic element 13E toward the first magnetic element 11E is along the third direction. The third direction crosses a plane including the first and second directions. The third direction is, for example, the Z-axis direction. The direction from the second magnetic element 12E toward the fourth magnetic element 14E is along the third direction.

In FIG. 10B, the positions of the first to fourth magnetic elements 11E to 14E are drawn as being shifted for easier viewing of the drawing. As shown in FIG. 10B, the first element portion 11e is electrically connected to the third element portion 13e. The second element portion 12e is electrically connected to the fourth element portion 14e. The first element other-portion 11f is electrically connected to the second element other-portion 12f. The third element other-portion 13f is electrically connected to the fourth element other-portion 14f. For example, these electrical connections are performed by the connection members 18a to 18d.

As shown in FIGS. 9B and 10A, the first conductive member 21 includes the first conductive portion 21a, the second conductive portion 21b, the first middle portion m1, and the second middle portion m2. The first middle portion m1 is between the first conductive portion 21a and the second conductive portion 21b in the second direction (the X-axis direction). The second middle portion m2 is between the first middle portion m1 and the second conductive portion 21b in the second direction.

As shown in FIG. 9B, the first middle portion m1 is between the third magnetic element 13E and the first magnetic element 11E in the third direction (e.g., the Z-axis direction). The second middle portion m2 is between the second magnetic element 12E and the fourth magnetic element 14E in the third direction.

As shown in FIG. 10A, the first circuit 71 is electrically connected to the first and second conductive portions 21a and 21b. For example, the electrical connection is performed by the connection members 28a and 28b, etc. The first circuit 71 is configured to supply the first current I1 including the alternating current component between the first conductive portion 21a and the second conductive portion 21b.

As shown in FIG. 10B, the second circuit 72 is electrically connected to the first connection point CP1 that is between the third element portion 13e and the first element portion 11e, and to the second connection point CP2 that is between the second element portion 12e and the fourth element portion 14e. For example, the electrical connections are performed by the connection members LCP1 and LCP2, etc. The second circuit 72 is configured to supply the second current I2 between the first connection point CP1 and the second connection point CP2.

The orientation (the phase) of the current magnetic field due to the first current I1 flowing through the first conductive member 21 is reversed between the first magnetic element 11E and the third magnetic element 13E. The orientation (the phase) of the current magnetic field due to the first current I1 flowing through the first conductive member 21 is reversed between the second magnetic element 12E and the fourth magnetic element 14E. For example, the effects of noise having a period that is 2 times the period of the alternating current component of the first current I1, etc., are suppressed by the bridge connection of four such magnetic elements. Detection is possible with higher accuracy.

As shown in FIG. 10B, the magnetic sensor 112 may include the third circuit 73. The third circuit 73 is electrically connected to the third connection point CP3 that is between the third element other-portion 13f and the fourth element other-portion 14f, and to the fourth connection point CP4 that is between the first element other-portion 11f and the second element other-portion 12f. The third circuit 73 is configured to detect the change ΔV of the potential between the third connection point CP3 and the fourth connection point CP4. The external magnetic field can be detected with higher sensitivity by the third circuit 73 detecting the change ΔV of the potential between the two midpoints of the bridge circuit.

The configuration of the magnetic sensor 111 is applicable to the magnetic sensor 112 within the extent of technical feasibility. For example, in the magnetic sensor 112, the first length L1 may be greater than the first cross length W1 (referring to FIG. 8). The second length L2 may be greater than the second cross length W2 (referring to FIG. 8). The third length L3 may be greater than the third cross length W3 (referring to FIG. 8). The fourth length L4 may be greater than the fourth cross length W4 (referring to FIG. 8).

Fourth Embodiment

Figure 11:
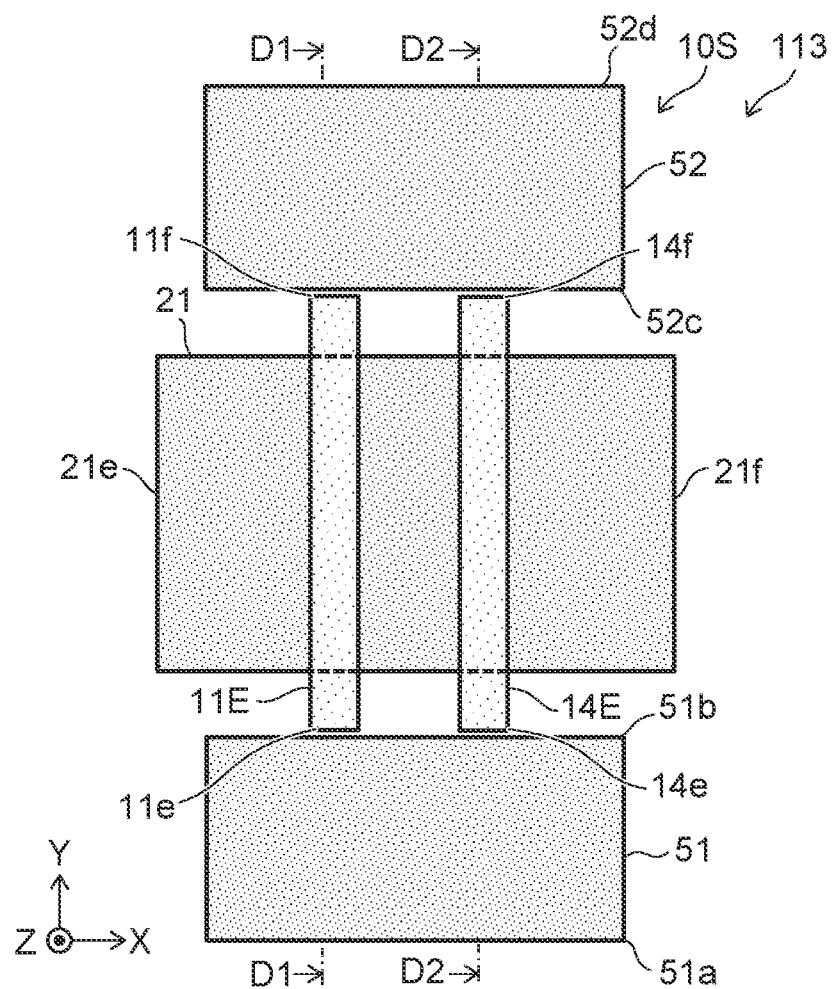
FIG. 11 is a schematic plan view illustrating a portion of a magnetic sensor according to a fourth embodiment.

FIG. 11 is a schematic plan view illustrating a portion of a magnetic sensor according to a fourth embodiment.

Figure 12A:
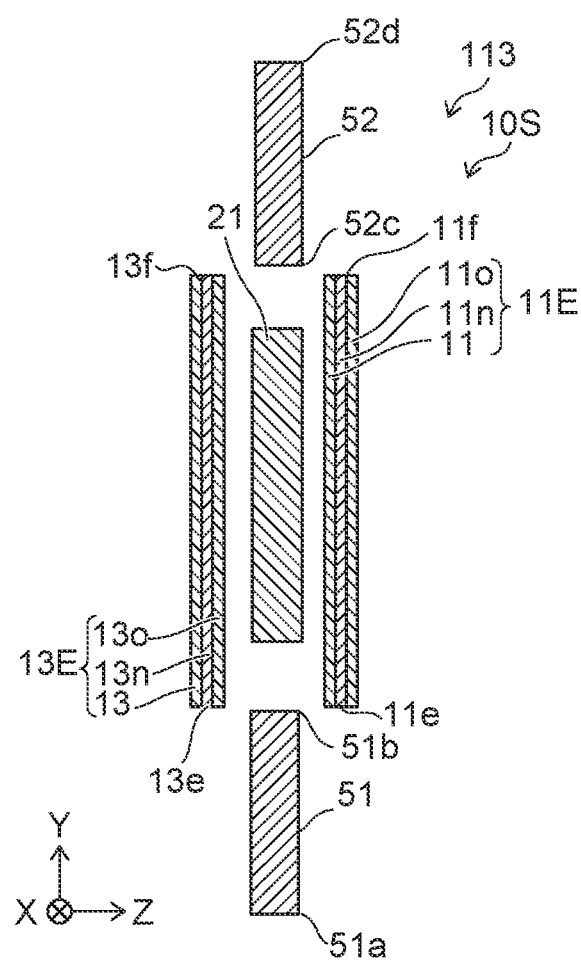
FIGS. 12A and 12B are schematic cross-sectional views illustrating a portion of the magnetic sensor according to the fourth embodiment.
Figure 12B:
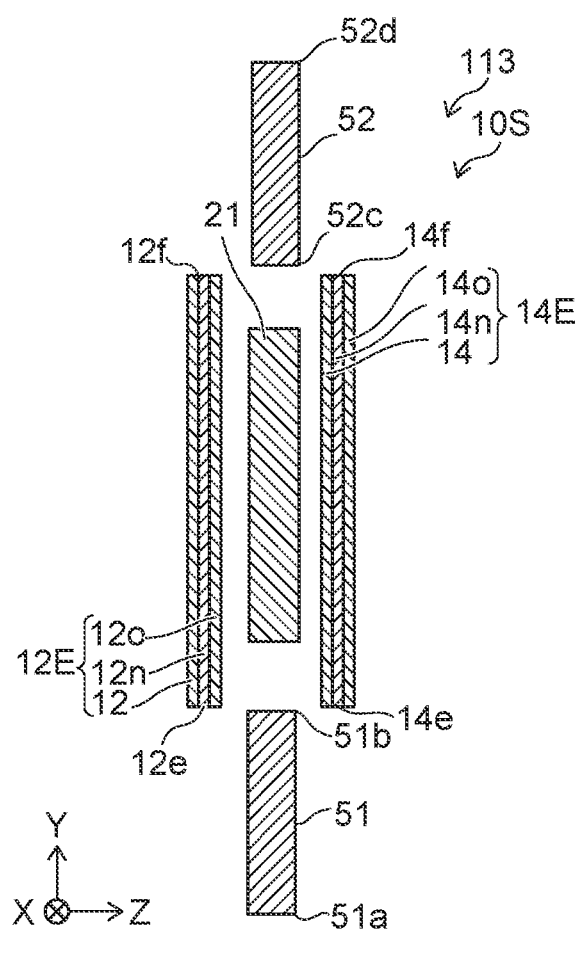

FIGS. 12A and 12B are schematic cross-sectional views illustrating a portion of the magnetic sensor according to the fourth embodiment.

FIG. 12A is a line D1-D1 cross-sectional view of FIG. 11.
FIG. 12B is a line D2-D2 cross-sectional view of FIG. 11.

As shown in FIG. 11, the magnetic sensor 113 includes a first magnetic member 51 and a second magnetic member 52. Otherwise, the configuration of the magnetic sensor 113 may be similar to that of the magnetic sensor 112.

The first magnetic member 51 includes a first magnetic end portion 51a and a second magnetic end portion 51b. The second magnetic member 52 includes a third magnetic end portion 52c and a fourth magnetic end portion 52d. The direction from the first magnetic end portion 51a toward the fourth magnetic end portion 52d is along the first direction (the Y-axis direction). The second magnetic end portion 51b is between the first magnetic end portion 51a and the fourth magnetic end portion 52d in the first direction. The third magnetic end portion 52c is between the second magnetic end portion 51b and the fourth magnetic end portion 52d in the first direction. The third magnetic end portion 52c is separated from the second magnetic end portion 51b in the first direction.

As shown in FIGS. 12A and 12B, at least a portion of the first conductive member 21 is between the second magnetic end portion 51b and the third magnetic end portion 52c in the first direction (the Y-axis direction).

For example, the position along the first direction (the Y-axis direction) of the first element portion 11e is between the position along the first direction of the second magnetic end portion 51b and the position along the first direction of the first element other-portion 11f. The position along the first direction of the first element other-portion 11f is between the position along the first direction of the first element portion 11e and the position along the first direction of the third magnetic end portion 52c.

For example, the position along the first direction (the Y-axis direction) of the third element portion 13e is between the position along the first direction of the second magnetic end portion 51b and the position along the first direction of the third element other-portion 13f. The position along the first direction of the third element other-portion 13f is between the position along the first direction of the third element portion 13e and the position along the first direction of the third magnetic end portion 52c.

For example, the first magnetic member 51 and the second magnetic member 52 function as MFCs (Magnetic Field Concentrators). For example, the MFCs concentrate the external magnetic field of the detection object. The concentrated external magnetic field is efficiently applied to the magnetic elements. Higher sensitivity is obtained.

The configuration described with reference to the magnetic sensor 110 is applicable to the magnetic sensors 111, 112, and 113.

Fifth Embodiment

FIGS. 13, 14A, 14B, and 15 are schematic views illustrating a magnetic sensor according to a fifth embodiment.

Figure 13:
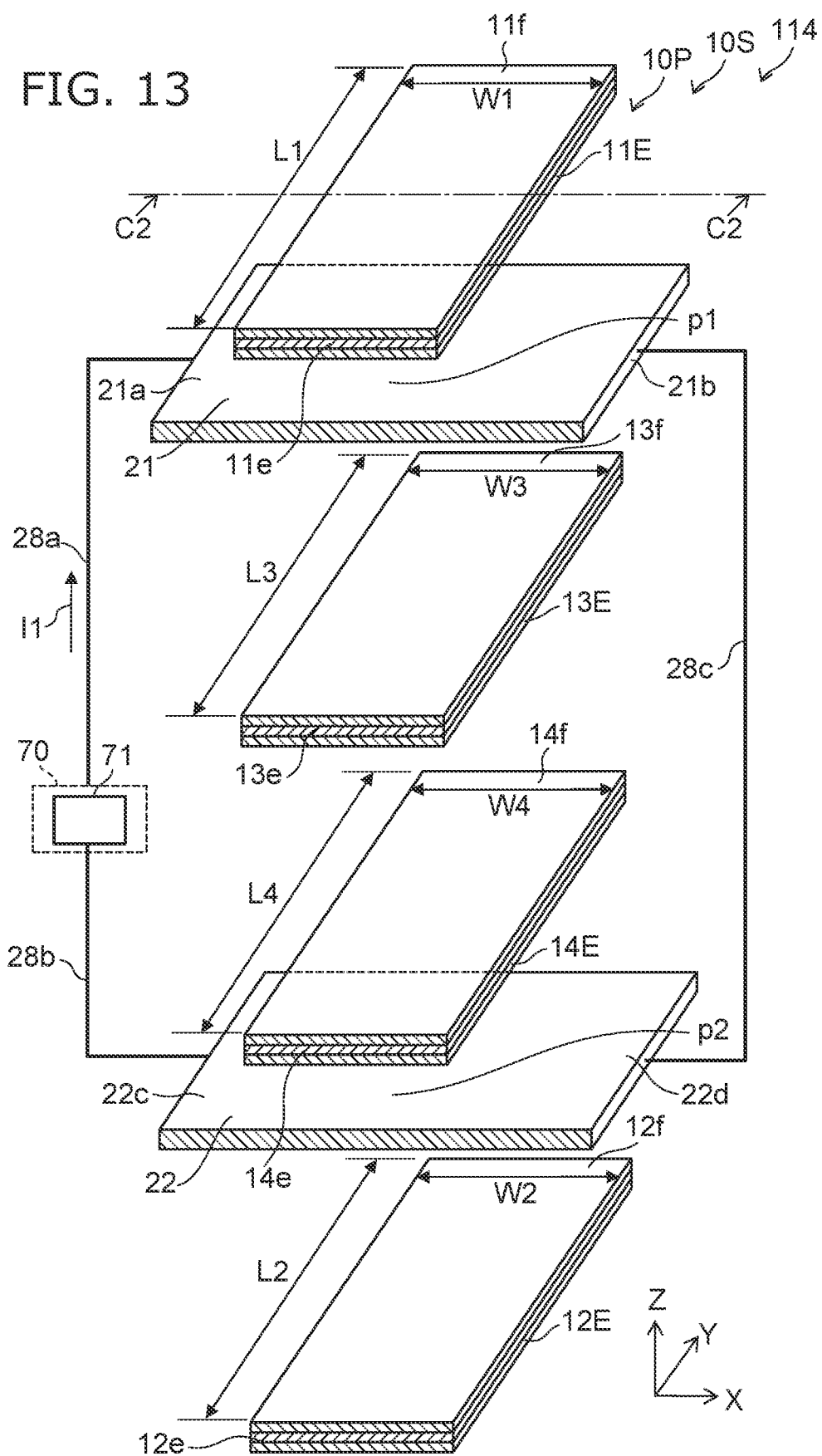
FIG. 13 is a schematic view illustrating a magnetic sensor according to a fifth embodiment.
Figure 14A:
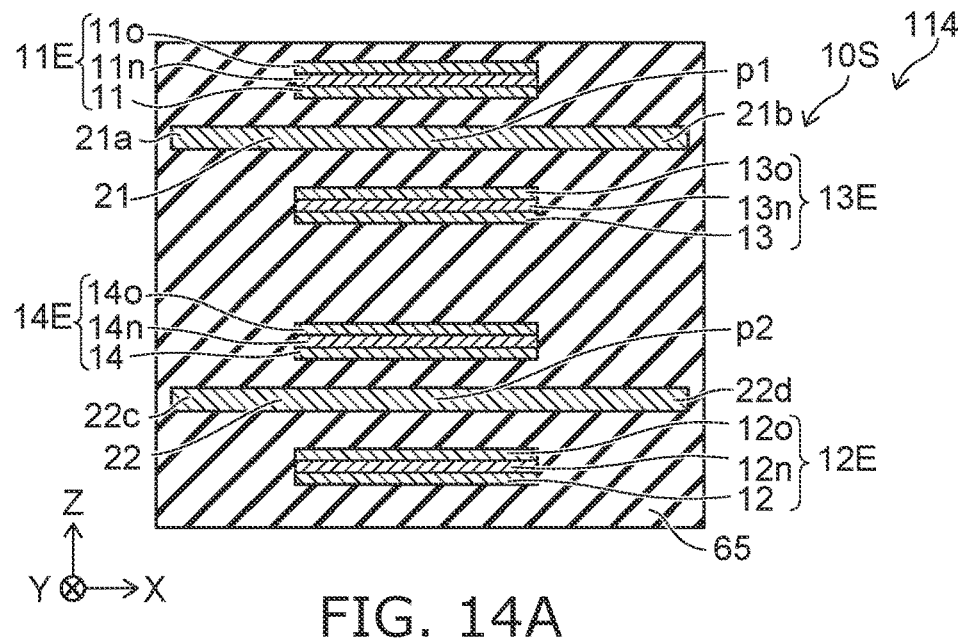
FIGS. 14A and 14B are schematic views illustrating a magnetic sensor according to a fifth embodiment.
Figure 14B:
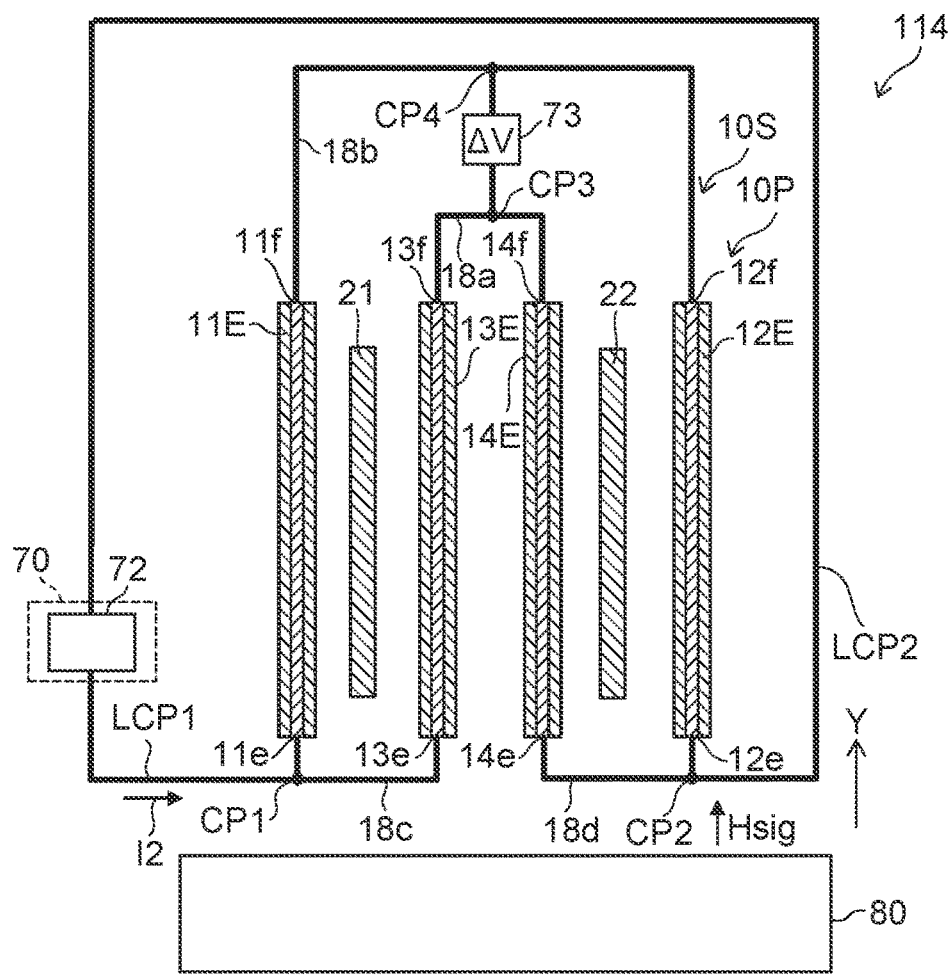
Figure 15:
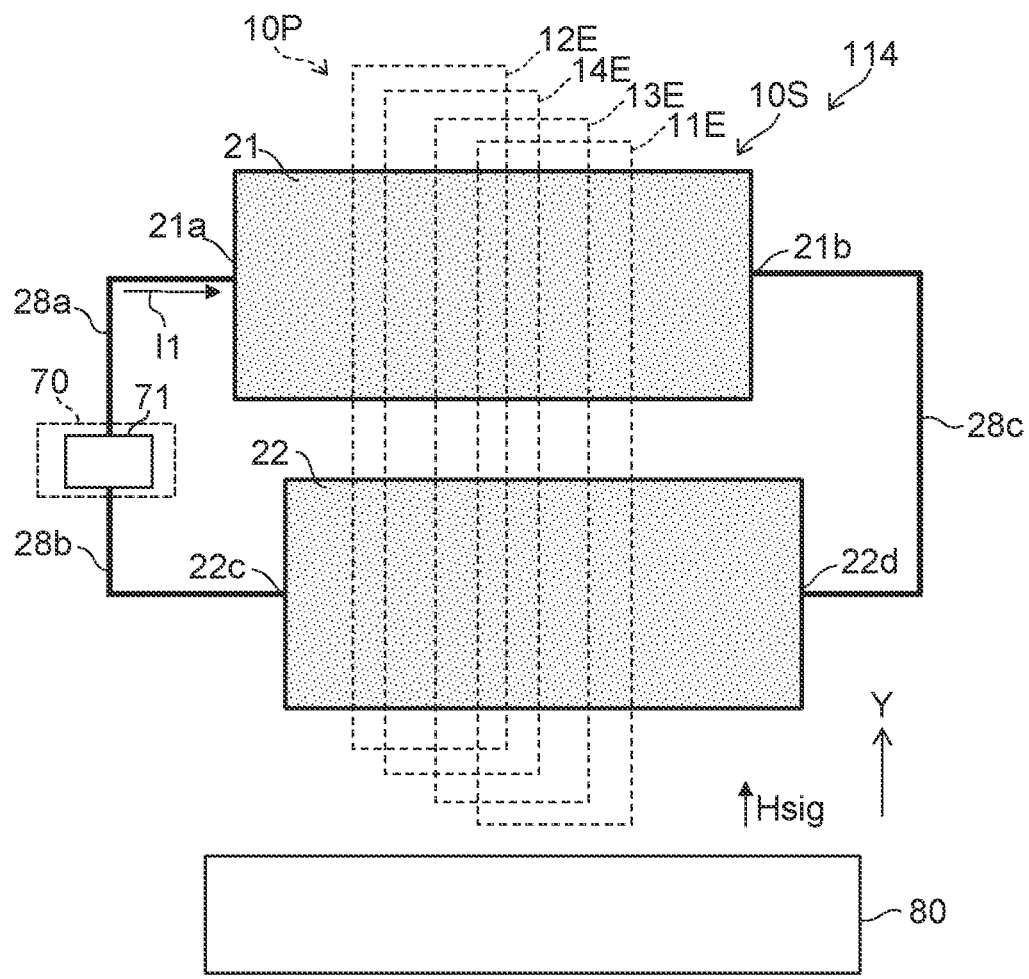
FIG. 15 is a schematic view illustrating a magnetic sensor according to a fifth embodiment.

FIG. 13 is a schematic perspective view. FIG. 14A is a line C2-C2 cross-sectional view of FIG. 13. FIG. 14B is a schematic cross-sectional view. FIG. 15 is a schematic plan view.

As shown in FIGS. 13 and 14B, the magnetic sensor 114 according to the embodiment includes the sensor part 10S, the first circuit 71, and the second circuit 72. The sensor part 10S includes the magnetic element part 10P, the first conductive member 21, and the second conductive member 22. In FIGS. 14A and 14B, some of the multiple components included in the magnetic sensor 114 are drawn as being separated from each other for easier viewing of the drawing.

As shown in FIG. 13, the magnetic element part 10P includes the first magnetic element 11E, the second magnetic element 12E, the third magnetic element 13E, and the fourth magnetic element 14E. The first magnetic element 11E includes the first element portion 11e and the first element other-portion 11f. The second magnetic element 12E includes the second element portion 12e and the second element other-portion 12f. The third magnetic element 13E includes the third element portion 13e and the third element other-portion 13f. The fourth magnetic element 14E includes the fourth element portion 14e and the fourth element other-portion 14f. The direction from the first element portion 11e toward the first element other-portion 11f, the direction from the second element portion 12e toward the second element other-portion 12f, the direction from the third element portion 13e toward the third element other-portion 13f, and the direction from the fourth element portion 14e toward the fourth element other-portion 14f are along the first direction. The first direction is, for example, the Y-axis direction.

As shown in FIG. 14B, the first element portion 11e is electrically connected to the third element portion 13e. The second element portion 12e is electrically connected to the fourth element portion 14e. The first element other-portion 11f is electrically connected to the second element other-portion 12f. The third element other-portion 13f is electrically connected to the fourth element other-portion 14f. For example, these electrical connections may be performed by the connection members 18a to 18d, etc.

As shown in FIG. 13, the first conductive member 21 includes the first conductive portion 21a, the second conductive portion 21b, and the first portion p1. The position of the first portion p1 in the second direction is between the position of the first conductive portion 21a in the second direction and the position of the second conductive portion 21b in the second direction. The second direction crosses the first direction. The second direction is, for example, the X-axis direction.

As shown in FIG. 13, the second conductive member 22 includes a third conductive portion 22c, the fourth conductive portion 22d, and the second portion p2. The position of the second portion p2 in the second direction is between the position of the third conductive portion 22c in the second direction and the position of the fourth conductive portion 22d in the second direction.

A direction that crosses a plane including the first and second directions is taken as the third direction. The third direction is, for example, the Z-axis direction. As shown in FIGS. 13 and 14A, the fourth magnetic element 14E is between the second magnetic element 12E and the first magnetic element 11E in the third direction. The third magnetic element 13E is between the fourth magnetic element 14E and the first magnetic element 11E in the third direction.

As shown in FIGS. 13 and 14A, the second portion p2 is between the second magnetic element 12E and the fourth magnetic element 14E in the third direction. The first portion p1 is between the third magnetic element 13E and the first magnetic element 11E in the third direction.

As shown in FIGS. 13 and 15, the fourth conductive portion 22d is electrically connected to the second conductive portion 21b. For example, the electrical connection may be performed by the connection member 28c, etc.

As shown in FIGS. 13 and 15, the first circuit 71 is electrically connected to the first and third conductive portions 21a and 22c. For example, the electrical connections may be performed by the connection members 28a and 28b, etc. The first circuit 71 is configured to supply the first current I1 including the alternating current component between the first conductive portion 21a and the third conductive portion 22c. The orientation of the first current I1 at the same time is reversed between the first conductive member 21 and the second conductive member 22. For example, currents that have reverse phases flow. For example, the first current I1 flows from the fourth conductive portion 22d toward the third conductive portion 22c when the first current I1 flows from the first conductive portion 21a toward the second conductive portion 21b.

As shown in FIG. 14B, the second circuit 72 is electrically connected to the first connection point CP1 that is between the first element portion 11e and the third element portion 13e, and to the second connection point CP2 that is between the second element portion 12e and the fourth element portion 14e. For example, the electrical connections may be performed by the connection members 28a and 28b, etc. The electrical connections may be performed by the connection members LCP1 and LCP2, etc. The second circuit 72 is configured to supply the second current I2 between the first connection point CP1 and the second connection point CP2.

In the magnetic sensor 114, the alternating current magnetic field that is due to the first current I1 that is supplied to the first and second conductive members 21 and 22 and includes the alternating current is applied to the first to fourth magnetic elements 11E to 14E in the +Y direction or the −Y direction. The orientation of the alternating current magnetic field applied to the first and second magnetic elements 11E and 12E and the orientation of the alternating current magnetic field applied to the third and fourth magnetic elements 13E and 14E are the reverse of each other at the same time. For example, when the orientation of the alternating current magnetic field applied to the first and second magnetic elements 11E and 12E is the +Y direction, the orientation of the alternating current magnetic field applied to the third and fourth magnetic elements 13E and 14E is the −Y direction. The external magnetic field can be detected with suppressed noise due to the bridge connection of four such magnetic elements. A magnetic sensor can be provided in which the sensitivity can be increased.

As shown in FIG. 13, the first magnetic element 11E has the first length L1 along the first direction (the Y-axis direction), and the first cross length W1 along the second direction (e.g., the X-axis direction). The first length L1 is greater than the first cross length W1. The second magnetic element 12E has the second length L2 along the first direction, and the second cross length W2 along the second direction. The second length L2 is greater than the second cross length W2. The third magnetic element 13E has the third length L3 along the first direction, and the third cross length W3 along the second direction. The third length L3 is greater than the third cross length W3. The fourth magnetic element 14E has the fourth length L4 along the first direction, and the fourth cross length W4 along the second direction. The fourth length L4 is greater than the fourth cross length W4. The magnetizations of the magnetic layers are favorably controlled.

For example, the magnetizations of the two magnetic layers included in the magnetic element in the state in which there is no external magnetic field can be stabilized in the ±X-directions by the magnetic field generated by the second current I2.

As shown in FIG. 14B, the magnetic sensor 114 may further include the third circuit 73. The third circuit 73 is electrically connected to the third connection point CP3 that is between the third element other-portion 13f and the fourth element other-portion 14f, and to the fourth connection point CP4 between the first element other-portion 11f and the second element other-portion 12f. The third circuit 73 is configured to detect the change ΔV of the potential between the third connection point CP3 and the fourth connection point CP4. For example, the signal magnetic field Hsig of the detection object 80 (referring to FIG. 14B) can be detected by the third circuit 73 with high sensitivity and with suppressed noise.

The configuration described with reference to the magnetic sensor 110 is applicable to the magnetic sensor 114. For example, as shown in FIG. 14A, the first magnetic element 11E includes the first magnetic layer 11, the first counter magnetic layer 11O, and the first nonmagnetic layer 11n provided between the first magnetic layer 11 and the first counter magnetic layer 110. For example, the second magnetic element 12E includes the second magnetic layer 12, the second counter magnetic layer 12o, and the second nonmagnetic layer 12n provided between the second magnetic layer 12 and the second counter magnetic layer 12o. For example, the third magnetic element 13E includes the third magnetic layer 13, the third counter magnetic layer 13o, and the third nonmagnetic layer 13n provided between the third magnetic layer 13 and the third counter magnetic layer 13o. For example, the fourth magnetic element 14E includes the fourth magnetic layer 14, the fourth counter magnetic layer 14o, and the fourth nonmagnetic layer 14n provided between the fourth magnetic layer 14 and the fourth counter magnetic layer 14o.

As shown in FIG. 14A, the insulating member 65 may be provided around the first to fourth magnetic elements 11E to 14E, the first conductive member 21, and the second conductive member 22.

Figure 16:
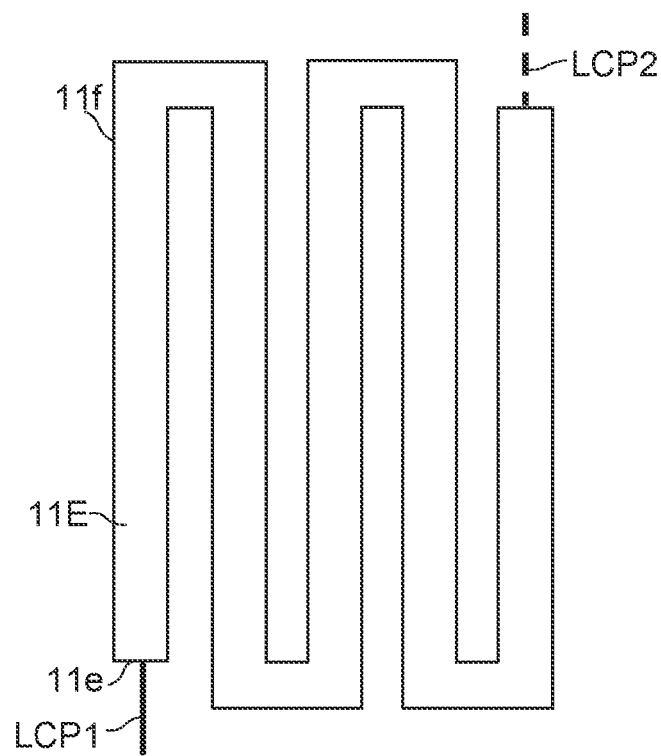
FIG. 16 is a schematic plan view illustrating a portion of a magnetic sensor according to the embodiment.

FIG. 16 is a schematic plan view illustrating a portion of a magnetic sensor according to the embodiment.

As shown in FIG. 16, the first magnetic element 11E may have a meandering structure. Other magnetic elements also may have meandering structures. For example, the length of the current path of the magnetic element can be increased thereby, and an appropriate resistance value is easily obtained. The electrical resistance of one magnetic element is, for example, not less than 100Ω and not more than 2 kΩ. For example, the circuit is simple because the appropriate resistance is obtained.

Figure 17:
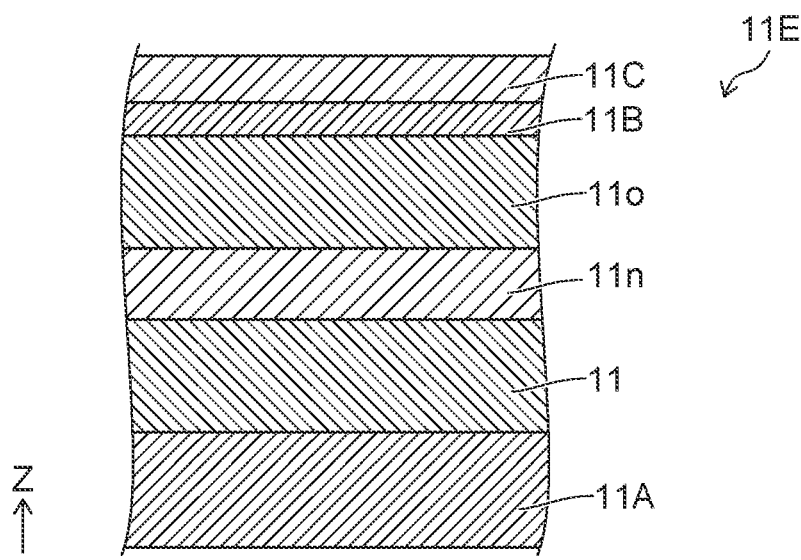
FIG. 17 is a schematic cross-sectional view illustrating a portion of the magnetic sensor according to the embodiment.

FIG. 17 is a schematic cross-sectional view illustrating a portion of the magnetic sensor according to the embodiment.

As shown in FIG. 17, the first magnetic element 11E may include a first oxide layer 11A and a second oxide layer 11B. The first magnetic layer 11 is between the first oxide layer 11A and the second oxide layer 11B. The first counter magnetic layer 110 is between the first magnetic layer 11 and the second oxide layer 11B. The first magnetic layer 11 contacts the first oxide layer 11A. The first counter magnetic layer 110 contacts the second oxide layer 11B. For example, a high MR ratio is obtained by the magnetic layers contacting the oxide layers.

The first oxide layer 11A may be, for example, a sapphire substrate. The second oxide layer 11B is, for example, TaO. At least one of the first magnetic layer 11 or the first counter magnetic layer 110 includes, for example, at least one selected from the group consisting of CoFe, NiFe, and CoFeNi. The first nonmagnetic layer 11n includes, for example, Cu.

The first magnetic element 11E may further include a layer 11C. The layer 11C is, for example, a Ta layer. The second oxide layer 11B is between the first counter magnetic layer 110 and the layer 11C.

The configuration of the first magnetic element 11E described above is applicable to the second to fourth magnetic elements 12E to 14E.

For example, the magnetic sensor according to the embodiment can be applied to an inspection device, etc. As described below, the inspection device may include a diagnostic device.

Figure 18:
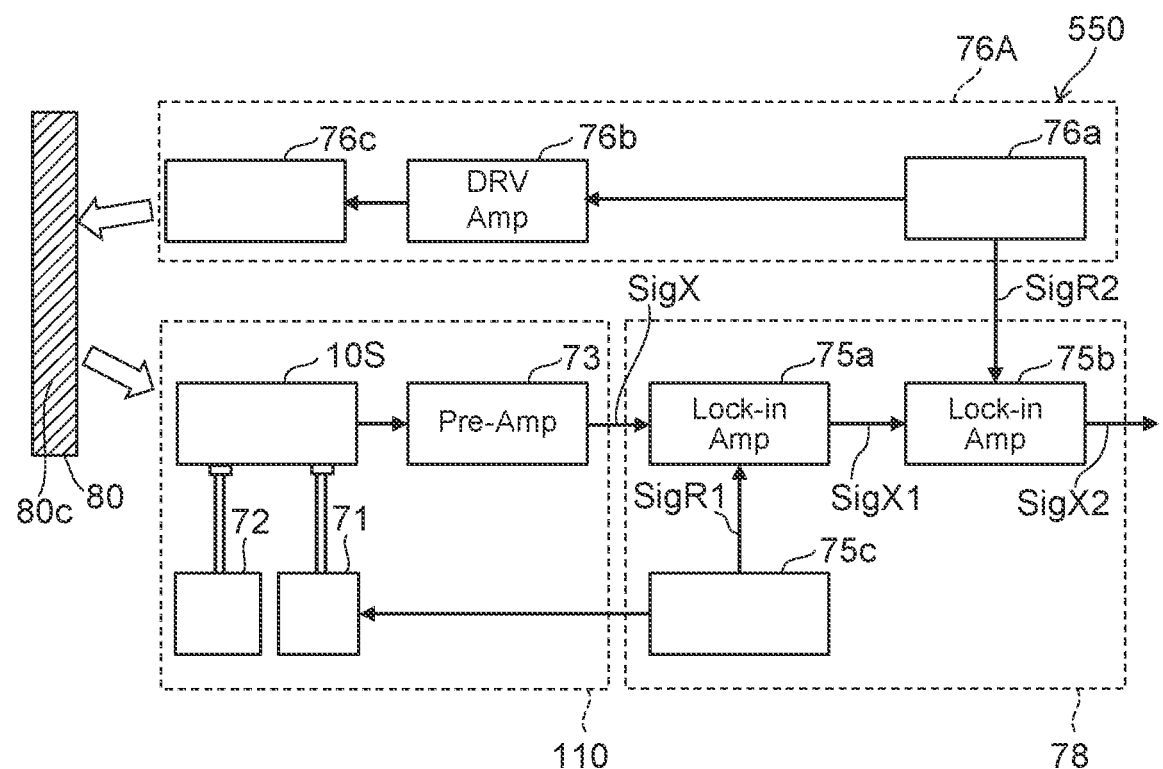
FIG. 18 is a schematic view illustrating an inspection device according to the embodiment.

FIG. 18 is a schematic view illustrating an inspection device according to the embodiment.

As shown in FIG. 18, an inspection device 550 according to the embodiment includes a processor 78 and the magnetic sensor (in the example of FIG. 18, the magnetic sensor 110) according to the embodiment. The processor 78 processes an output signal SigX obtained from the magnetic sensor 110.

In the example, the processor 78 includes a sensor controller 75c, a first lock-in amplifier 75a, and a second lock-in amplifier 75b. For example, the first circuit 71 is controlled by the sensor controller 75c; and the first current I1 including the alternating current component (referring to FIG. 2A, etc.) is supplied from the first circuit 71 to the sensor part 10S. The frequency of the alternating current component of the first current I1 is, for example, not more than 100 kHz. The second current I2 (referring to FIG. 2B, etc.) is supplied from the second circuit 72 to the sensor part 10S. The change ΔV (referring to FIG. 2B) of the potential of the magnetic element part 10P of the sensor part 10S (referring to FIG. 2B) is detected by the third circuit 73. For example, the output of the third circuit 73 is the output signal SigX.

In the example, the inspection device 550 includes a magnetic field application part 76A. The magnetic field application part 76A is configured to apply a magnetic field to the detection object 80. The detection object 80 is, for example, the inspection object. The detection object 80 includes at least an inspection conductive member 80c such as a metal, etc. For example, an eddy current is generated in the inspection conductive member 80c when the magnetic field is applied to the inspection conductive member 80c by the magnetic field application part 76A. The state of the eddy current changes when there is a flaw or the like in the inspection conductive member 80c. The state (e.g., the flaw, etc.) of the inspection conductive member 80c can be inspected by the magnetic sensor 110 detecting the magnetic field due to the eddy current. The magnetic field application part 76A is, for example, an eddy current generator.

In the example, the magnetic field application part 76A includes an application controller 76a, a drive amplifier 76b, and a coil 76c. A current is supplied to the drive amplifier 76b by the control by the application controller 76a. The current is, for example, an alternating current. The frequency of the current is, for example, an eddy current excitation frequency. The eddy current excitation frequency is, for example, not less than 10 Hz and not more than 100 kHz. The eddy current excitation frequency may be, for example, less than 100 kHz.

For example, information (which may be, for example, a signal) that relates to the frequency of the alternating current component of the first current I1 is supplied from the sensor controller 75c to the first lock-in amplifier 75a as a reference wave (a reference signal). The output of the first lock-in amplifier 75a is supplied to the second lock-in amplifier 75b. Information (which may be, for example, a signal) that relates to the eddy current excitation frequency is supplied from the application controller 76a to the second lock-in amplifier 75b as a reference wave (a reference signal). The second lock-in amplifier 75b is configured to output a signal component corresponding to the eddy current excitation frequency.

Thus, for example, the processor 78 includes the first lock-in amplifier 75a. The output signal SigX that is obtained from the magnetic sensor 110 and a signal SigR1 that corresponds to the frequency of the alternating current component included in the first current I1 are input to the first lock-in amplifier 75a. The first lock-in amplifier 75a is configured to output an output signal SigX1 that has the signal SigR1 corresponding to the frequency of the alternating current component included in the first current I1 as the reference wave (the reference signal). By providing the first lock-in amplifier 75a, it is possible to suppress the noise and detect with high sensitivity.

The processor 78 may further include the second lock-in amplifier 75b. The output signal SigX1 of the first lock-in amplifier 75a and a signal SigR2 that corresponds to the frequency (the eddy current excitation frequency) of the supply signal (in the example, the magnetic field due to the magnetic field application part 76A) supplied toward the inspection object 80 are input to the second lock-in amplifier 75b. The second lock-in amplifier 75b is configured to output an output signal SigX2 that uses the signal SigR2 corresponding to the frequency of the supply signal supplied toward the inspection object 80 as a reference wave (a reference signal). By providing the second lock-in amplifier 75b, it is possible to detect with more noise suppression and with even higher sensitivity.

An abnormality such as a flaw or the like of the inspection conductive member 80c of the detection object 80 can be inspected by the inspection device 550.

Figure 19:
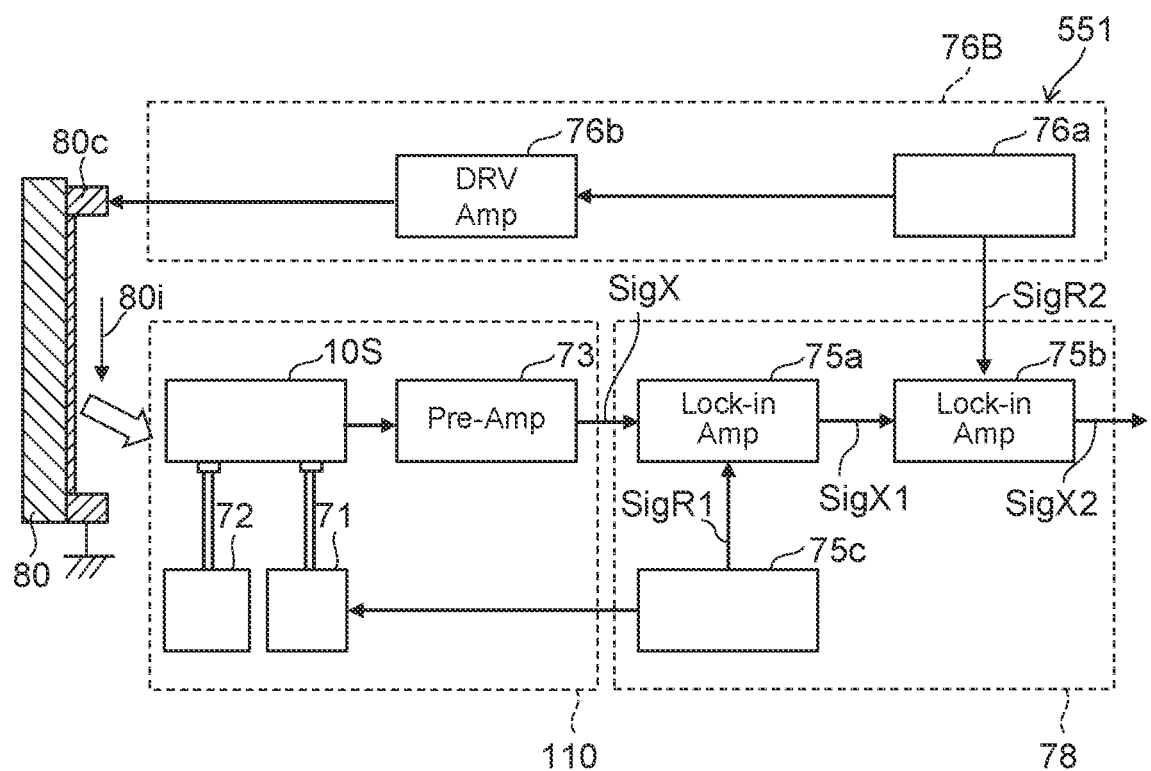
FIG. 19 is a schematic view illustrating an inspection device according to the embodiment.

FIG. 19 is a schematic view illustrating an inspection device according to the embodiment.

As shown in FIG. 19, the inspection device 551 according to the embodiment includes the processor 78 and the magnetic sensor (in the example of FIG. 19, the magnetic sensor 110) according to the embodiment. The configurations of the magnetic sensor and the processor 78 of the inspection device 551 may be similar to those of the inspection device 550. In the example, the inspection device 551 includes a detection object driver 76B. The detection object driver 76B is configured to supply a current to the inspection conductive member 80c included in the detection object 80. The inspection conductive member 80c is, for example, wiring included in the detection object 80. A magnetic field that is due to a current 80i flowing in the inspection conductive member 80c is detected by the magnetic sensor 110. The inspection conductive member 80c can be inspected based on an abnormality due to the detection result of the magnetic sensor 110. The detection object 80 may be, for example, an electronic device such as a semiconductor device, etc. The detection object 80 may be, for example, a battery, etc.

In the example, the detection object driver 76B includes the application controller 76a and the drive amplifier 76b. The drive amplifier 76b is controlled by the application controller 76a; and the current is supplied from the drive amplifier 76b to the inspection conductive member 80c. The current is, for example, an alternating current. For example, the alternating current is supplied to the inspection conductive member 80c. The frequency of the alternating current is, for example, not less than 10 Hz and not more than 100 kHz. The frequency may be, for example, less than 100 kHz. In the example as well, for example, by providing the first lock-in amplifier 75a and the second lock-in amplifier 75b, it is possible to suppress the noise and detect with high sensitivity. In one example of the inspection device 551, multiple magnetic sensors (e.g., the multiple magnetic sensors 110) may be provided. The multiple magnetic sensors are, for example, a sensor array. The inspection conductive member 80c can be inspected in a short period of time by the sensor array. In one example of the inspection device 551, the inspection conductive member 80c may be inspected by scanning the magnetic sensor (e.g., the magnetic sensor 110).

An example of an application of the magnetic sensor according to the embodiment will now be described.

Figure 20:
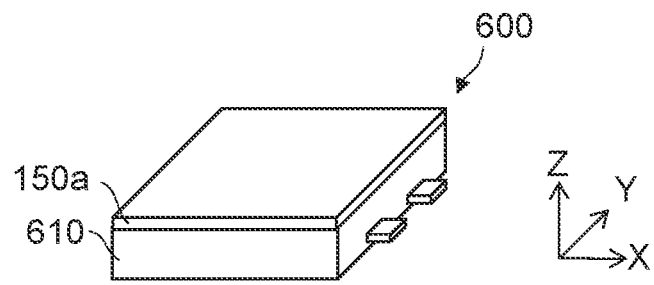
FIG. 20 is a schematic perspective view showing an application example of the magnetic sensor according to the embodiment.

FIG. 20 is a schematic perspective view showing an application example of the magnetic sensor according to the embodiment.

Figure 21:
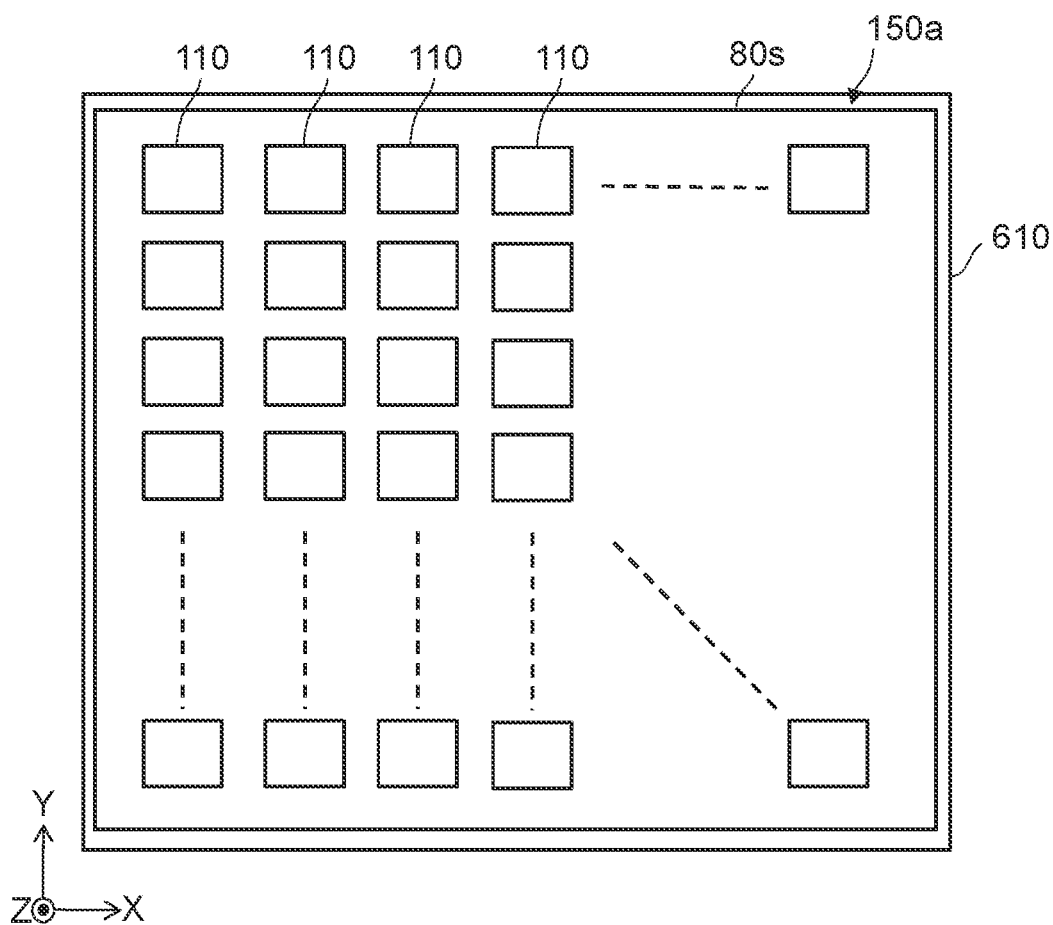
FIG. 21 is a schematic plan view showing the application example of the magnetic sensor according to the embodiment.

FIG. 21 is a schematic plan view showing the application example of the magnetic sensor according to the embodiment.

As shown in FIGS. 20 and 21, the magnetic sensor 150a according to the embodiment may be used with a battery 610. For example, a battery system 600 includes the battery 610 and the magnetic sensor 150a. The magnetic sensor 150a can detect a magnetic field generated by a current flowing in the battery 610.

For example, as shown in FIG. 21, the magnetic sensor 150a includes multiple magnetic sensors according to the embodiment. In the example, the magnetic sensor 150a includes the multiple magnetic sensors 110 (or 120, 130, etc.). For example, the multiple magnetic sensors are arranged along two directions (e.g., the X-axis direction and the Y-axis direction). For example, the multiple magnetic sensors 110 are located on a substrate.

The magnetic sensor 150a can detect the magnetic field generated by the current flowing in the battery 610. For example, there are cases where an abnormal current flows in the battery 610 when the battery 610 approaches an abnormal state. The change of the state of the battery 610 can be known by the magnetic sensor 150a detecting the abnormal current. For example, the entire battery 610 can be inspected in a short period of time by using bidirectional sensor group drive means in a state in which the magnetic sensor 150a is located proximate to the battery 610. The magnetic sensor 150a may be used to inspect the battery 610 in the manufacturing of the battery 610.

An example of a diagnostic device that uses a magnetic sensor according to the embodiment will now be described.

Figure 22:
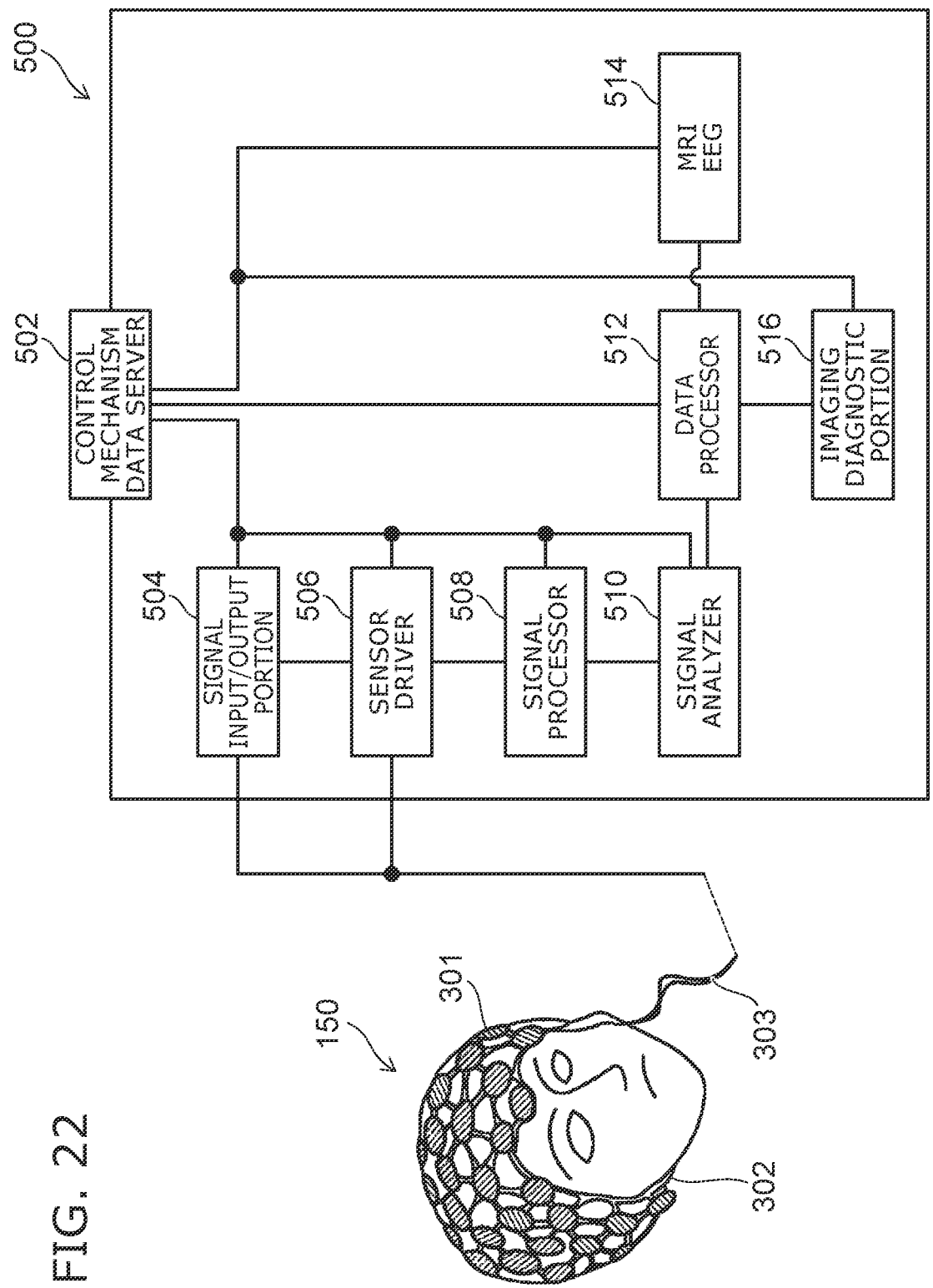
FIG. 22 is a schematic view showing the magnetic sensor and the diagnostic device according to the embodiment.

FIG. 22 is a schematic view showing the magnetic sensor and the diagnostic device according to the embodiment.

As shown in FIG. 22, the diagnostic device 500 includes the magnetic sensor 150. The magnetic sensor 150 includes the magnetic sensors described in reference to the first to fourth embodiments and modifications of the magnetic sensors. The diagnostic device 500 is an example of an inspection device.

In the diagnostic device 500, the magnetic sensor 150 is, for example, a magnetoencephalograph device. The magnetoencephalograph device detects a magnetic field generated by cranial nerves. When the magnetic sensor 150 is included in a magnetoencephalograph device, the size of the magnetic element included in the magnetic sensor 150 is, for example, not less than 1 mm but less than 10 mm. The size is, for example, the length including the MFC.

As shown in FIG. 22, the magnetic sensor 150 (the magnetoencephalograph device) is mounted to, for example, the head of a human body. The magnetic sensor 150 (the magnetoencephalograph device) includes a sensor part 301. The magnetic sensor 150 (the magnetoencephalograph device) may include multiple sensor parts 301. The number of the multiple sensor parts 301 is, for example, about 100 (e.g., not less than 50 and not more than 150). The multiple sensor parts 301 are provided in a base body 302 that is pliable.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 (the magnetic sensors described in reference to the first and second embodiments) is small compared to the size of a conventional SQUID magnetic sensor. Therefore, the mounting of the multiple sensor parts 301 is easy. The mounting of the multiple sensor parts 301 and the other circuits is easy. It is easy for the multiple sensor parts 301 and the other sensors to coexist.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected to a sensor driver 506 and a signal input/output part 504 of the diagnostic device 500. Magnetic field measurement is performed in the sensor part 301 based on the electrical power from the sensor driver 506 and the control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, etc., is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 22, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be pliable or may be substantially not pliable. In the example shown in FIG. 22, the base body 302 is a continuous film that is patterned into a hat-like configuration. The base body 302 may have a net configuration. For example, good wearability is obtained thereby. For example, the adhesion of the base body 302 to the human body is improved. The base body 302 may have a hard helmet-like configuration.

Figure 23:
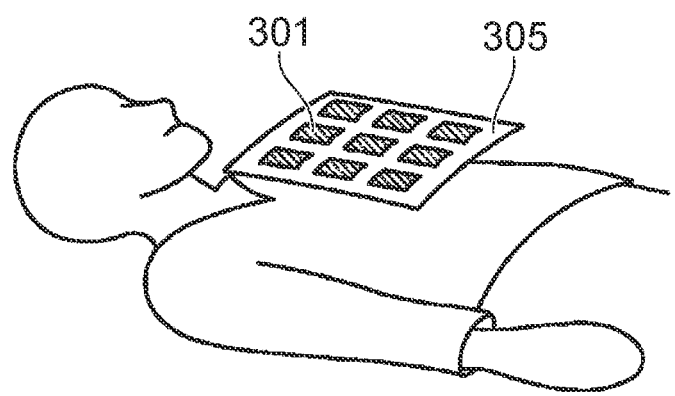
FIG. 23 is a schematic view showing the magnetic sensor according to the embodiment.

FIG. 23 is a schematic view showing the magnetic sensor according to the embodiment.

FIG. 23 is an example of a magnetic detection instrument. In the example shown in FIG. 23, the sensor part 301 is provided on a hard base body 305 having a flat plate shape.

The input and output of the signal obtained from the sensor part 301 in the example shown in FIG. 23 are similar to the input and output described with reference to FIG. 22. The processing of the signal obtained from the sensor part 301 in the example shown in FIG. 23 is similar to the processing described with reference to FIG. 22.

There is a reference example in which a SQUID (Superconducting Quantum Interference Device) magnetic sensor is used as a device to measure a faint magnetic field such as a magnetic field generated from a living body, etc. Because superconductivity is used in the reference example, the device is large; and the power consumption is large. The load on the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:
    a sensor part including a magnetic element part, a first conductive member, and a second conductive member,
        the magnetic element part including a first magnetic element, a second magnetic element, a third magnetic element, and a fourth magnetic element,
        the first magnetic element including a first element portion and a first element other-portion,
        the second magnetic element including a second element portion and a second element other-portion,
        the third magnetic element including a third element portion and a third element other-portion,
        the fourth magnetic element including a fourth element portion and a fourth element other-portion,
        the first element other-portion being between the first element portion and the second element other-portion in a first direction,
        the second element portion being between the first element other-portion and the second element other-portion in the first direction,
        the third element other-portion being between the third element portion and the fourth element other-portion in the first direction,
        the fourth element portion being between the third element other-portion and the fourth element other-portion in the first direction,
        the first element other-portion being electrically connected to the second element portion,
        the third element other-portion being electrically connected to the fourth element portion,
        the first element portion being electrically connected to the third element portion,
        the second element other-portion being electrically connected to the fourth element other-portion,
        the first conductive member including a first conductive portion, a second conductive portion, a third conductive portion, a first middle portion, and a second middle portion, a direction from the second conductive portion toward the first conductive portion being along a second direction crossing the first direction, the third conductive portion being between the first conductive portion and the second conductive portion, the first middle portion being between the first conductive portion and the third conductive portion, the second middle portion being between the third conductive portion and the second conductive portion, a direction from the first magnetic element toward the second middle portion being along a third direction crossing a plane including the first and second directions, a direction from the third magnetic element toward the first middle portion being along the third direction, the second conductive member including a fourth conductive portion, a fifth conductive portion, a sixth conductive portion, a third middle portion, and a fourth middle portion, a direction from the fifth conductive portion toward the fourth conductive portion being along the second direction, the sixth conductive portion being between the fifth conductive portion and the fourth conductive portion, the third middle portion being between the fourth conductive portion and the sixth conductive portion, the fourth middle portion being between the sixth conductive portion and the fifth conductive portion, a direction from the second magnetic element toward the fourth middle portion being along the third direction, a direction from the fourth magnetic element toward the third middle portion being along the third direction, the first conductive portion being electrically connected to the fourth conductive portion, the second conductive portion being electrically connected to the fifth conductive portion;

a first circuit electrically connected to the third and sixth conductive portions, the first circuit being configured to supply a first current between the third conductive portion and the sixth conductive portion, the first current including an alternating current component; and a second circuit electrically connected to a first connection point and a second connection point, the first connection point being between the first element portion and the third element portion, the second connection point being between the second element other-portion and the fourth element other-portion, the second circuit being configured to supply a second current between the first connection point and the second connection point.

Configuration 2

The magnetic sensor according to Configuration 1, further comprising:

a third circuit, the third circuit being electrically connected to a third connection point and a fourth connection point, the third connection point being between the first element other-portion and the second element portion, the fourth connection point being between the third element other-portion and the fourth element portion, the third circuit being configured to detect a change of a potential between the third connection point and the fourth connection point.

Configuration 3

The magnetic sensor according to Configuration 1 or 2, wherein the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction and a fourth cross length along the second direction, and the fourth length is greater than the fourth cross length.

Configuration 4

The magnetic sensor according to any one of Configurations 1 to 3, further comprising:

a first conductive layer;

a second conductive layer; and a fourth circuit, the first conductive layer overlapping the first and third magnetic elements in the third direction, the second conductive layer overlapping the second and fourth magnetic elements in the third direction, the first conductive layer including a first conductive layer end portion and a second conductive layer end portion, an orientation from the second conductive layer end portion toward the first conductive layer end portion being along the second direction, the second conductive layer including a third conductive layer end portion and a fourth conductive layer end portion, an orientation from the fourth conductive layer end portion toward the third conductive layer end portion being along the second direction, the first conductive layer end portion being electrically connected to the third conductive layer end portion, the second conductive layer end portion being electrically connected to the fourth conductive layer end portion, the fourth circuit being configured to supply a third current between a fifth connection point and a sixth connection point, the fifth connection point being between the first conductive layer end portion and the third conductive layer end portion, the sixth connection point being between the second conductive layer end portion and the fourth conductive layer end portion.

Configuration 5

The magnetic sensor according to any one of Configurations 1 to 4, wherein the first middle portion is between the third magnetic element and a portion of the first conductive layer, the second middle portion is between the first magnetic element and an other portion of the first conductive layer, the third middle portion is between the fourth magnetic element and a portion of the second conductive layer, and the fourth middle portion is between the second magnetic element and an other portion of the second conductive layer.

Configuration 6

The magnetic sensor according to any one of Configurations 1 to 5, wherein a direction from the first magnetic element toward the third magnetic element is along the second direction, and a direction from the second magnetic element toward the fourth magnetic element is along the second direction.

Configuration 7

A magnetic sensor, comprising:

a sensor part including a magnetic element part and a first conductive member, the magnetic element part including a first magnetic element, a second magnetic element, a third magnetic element, and a fourth magnetic element, the first magnetic element including a first element portion and a first element other-portion, the second magnetic element including a second element portion and a second element other-portion, the third magnetic element including a third element portion and a third element other-portion, the fourth magnetic element including a fourth element portion and a fourth element other-portion, a direction from the first element portion toward the first element other-portion, a direction from the second element portion toward the second element other-portion, a direction from the third element portion toward the third element other-portion, and a direction from the fourth element portion toward the fourth element other-portion being along a first direction, the first element portion being electrically connected to the second element portion, the third element portion being electrically connected to the fourth element portion, the first element other-portion being electrically connected to the fourth element other-portion, the second element other-portion being electrically connected to the third element other-portion, the first conductive member including a first conductive portion, a second conductive portion, a first portion, a second portion, a third portion, and a fourth portion, a position in a second direction of the first portion being between a position in the second direction of the first conductive portion and a position in the second direction of the second conductive portion, the second direction crossing the first direction, a position in the second direction of the second portion being between the position in the second direction of the first portion and the position in the second direction of the second conductive portion, a position in the second direction of the third portion being between the position in the second direction of the second portion and the position in the second direction of the second conductive portion, a position in the second direction of the fourth portion being between the position in the second direction of the third portion and the position in the second direction of the second conductive portion, a first orientation from the first magnetic element toward the first portion being along a third direction crossing a plane including the first and second directions, a second orientation from the second magnetic element toward the second portion being a reverse of the first orientation, a third orientation from the third magnetic element toward the third portion being a same as the first orientation, a fourth orientation from the fourth magnetic element toward the fourth portion being a reverse of the first orientation;

a first circuit electrically connected to the first and second conductive portions, the first circuit being configured to supply a first current between the first conductive portion and the second conductive portion, the first current including an alternating current component; and a second circuit electrically connected to a first connection point and a second connection point, the first connection point being between the first element portion and the second element portion, the second connection point being between the third element portion and the fourth element portion, the second circuit being configured to supply a second current between the first connection point and the second connection point.

Configuration 8

The sensor according to Configuration 7, wherein the first conductive member further includes a first middle portion, a second middle portion, and a third middle portion, the first middle portion is between the first magnetic element and the second magnetic element in the second direction, the second middle portion is between the second magnetic element and the third magnetic element in the second direction, and the third middle portion is between the third magnetic element and the fourth magnetic element in the second direction.

Configuration 9

The magnetic sensor according to Configuration 7 or 8, wherein the second magnetic element is between the first magnetic element and the fourth magnetic element in the second direction, and the third magnetic element is between the second magnetic element and the fourth magnetic element in the second direction.

Configuration 10

The magnetic sensor according to any one of Configurations 7 to 9, wherein the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction, and a fourth cross length along the second direction, and the fourth length is greater than the fourth cross length.

Configuration 11

The magnetic sensor according to any one of Configurations 7 to 10, further comprising:

a third circuit, the third circuit being electrically connected to a third connection point and a fourth connection point, the third connection point being between the first element other-portion and the fourth element other-portion, the fourth connection point being between the second element other-portion and the third element other-portion, the third circuit being configured to detect a change of a potential between the third connection point and the fourth connection point.

Configuration 12

A magnetic sensor, comprising:

a sensor part including a magnetic element part and a first conductive member, the magnetic element part including a first magnetic element, a second magnetic element, a third magnetic element, and a fourth magnetic element, the first magnetic element including a first element portion and a first element other-portion, the second magnetic element including a second element portion and a second element other-portion, the third magnetic element including a third element portion and a third element other-portion, the fourth magnetic element including a fourth element portion and a fourth element other-portion, a direction from the first element portion toward the first element other-portion, a direction from the second element portion toward the second element other-portion, a direction from the third element portion toward the third element other-portion, and a direction from the fourth element portion toward the fourth element other-portion being along a first direction, a second direction from the first magnetic element toward the fourth magnetic element crossing the first direction, a direction from the third magnetic element toward the second magnetic element being along the second direction, a direction from the third magnetic element toward the first magnetic element being along a third direction crossing a plane including the first and second directions, a direction from the second magnetic element toward the fourth magnetic element being along the third direction, the first element portion being electrically connected to the third element portion, the second element portion being electrically connected to the fourth element portion, the first element other-portion being electrically connected to the second element other-portion, the third element other-portion being electrically connected to the fourth element other-portion, the first conductive member including a first conductive portion, a second conductive portion, a first middle portion, and a second middle portion, the first middle portion being between the first conductive portion and the second conductive portion in the second direction, the second middle portion being between the first middle portion and the second conductive portion in the second direction, the first middle portion being between the third magnetic element and the first magnetic element in the third direction, the second middle portion being between the second magnetic element and the fourth magnetic element in the third direction;

a first circuit electrically connected to the first and second conductive portions, the first circuit being configured to supply a first current between the first conductive portion and the second conductive portion, the first current including an alternating current component; and a second circuit electrically connected to a first connection point and a second connection point, the first connection point being between the third element portion and the first element portion, the second connection point being between the second element portion and the fourth element portion, the second circuit being configured to supply a second current between the first connection point and the second connection point.

Configuration 13

The magnetic sensor according to Configuration 12, further comprising:

a third circuit, the third circuit being electrically connected to a third connection point and a fourth connection point, the third connection point being between the third element other-portion and the fourth element other-portion, the fourth connection point being between the first element other-portion and the second element other-portion, the third circuit being configured to detect a change of a potential between the third connection point and the fourth connection point.

Configuration 14

The magnetic sensor according to Configuration 12 or 13, wherein the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction, and a fourth cross length along the second direction, and the fourth length is greater than the fourth cross length.

Configuration 15

The magnetic sensor according to any one of Configurations 12 to 14, further comprising:

a first magnetic member including a first magnetic end portion and a second magnetic end portion; and a second magnetic member including a third magnetic end portion and a fourth magnetic end portion, a direction from the first magnetic end portion toward the fourth magnetic end portion being along the first direction, the second magnetic end portion being between the first magnetic end portion and the fourth magnetic end portion in the first direction, the third magnetic end portion being between the second magnetic end portion and the fourth magnetic end portion in the first direction, the third magnetic end portion being separated from the second magnetic end portion in the first direction, at least a portion of the first conductive member in the first direction being between the second magnetic end portion and the third magnetic end portion.

Configuration 16

A magnetic sensor, comprising:

a sensor part including a magnetic element part, a first conductive member, and a second conductive member, the magnetic element part including a first magnetic element, a second magnetic element, a third magnetic element, and a fourth magnetic element, the first magnetic element including a first element portion and a first element other-portion, the second magnetic element including a second element portion and a second element other-portion, the third magnetic element including a third element portion and a third element other-portion, the fourth magnetic element including a fourth element portion and a fourth element other-portion, a direction from the first element portion toward the first element other-portion, a direction from the second element portion toward the second element other-portion, a direction from the third element portion toward the third element other-portion, and a direction from the fourth element portion toward the fourth element other-portion being along a first direction, the first element portion being electrically connected to the third element portion, the second element portion being electrically connected to the fourth element portion, the first element other-portion being electrically connected to the second element other-portion, the third element other-portion being electrically connected to the fourth element other-portion, the first conductive member including a first conductive portion, a second conductive portion, and a first portion, a position of the first portion in a second direction being between a position of the first conductive portion in the second direction and a position of the second conductive portion in the second direction, the second direction crossing the first direction, the second conductive member including a third conductive portion, a fourth conductive portion, and a second portion, a position of the second portion in the second direction being between a position of the third conductive portion in the second direction and a position of the fourth conductive portion in the second direction, the fourth magnetic element being between the second magnetic element and the first magnetic element in a third direction crossing a plane including the first and second directions, the third magnetic element being between the fourth magnetic element and the first magnetic element in the third direction, the second portion being between the second magnetic element and the fourth magnetic element in the third direction, the first portion being between the third magnetic element and the first magnetic element in the third direction, the fourth conductive portion being electrically connected to the second conductive portion;

a first circuit electrically connected to the first and third conductive portions, the first circuit being configured to supply a first current between the first conductive portion and the third conductive portion, the first current including an alternating current component; and a second circuit electrically connected to a first connection point and a second connection point, the first connection point being between the first element portion and the third element portion, the second connection point being between the second element portion and the fourth element portion, the second circuit being configured to supply a second current between the first connection point and the second connection point.

Configuration 17

The magnetic sensor according to Configuration 16, wherein the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction, and a fourth cross length along the second direction, and the fourth length is greater than the fourth cross length.

Configuration 18

The magnetic sensor according to any one of Configurations 1 to 17, wherein an electrical resistance of the first magnetic element has a peak when a current supplied to the first magnetic element has a first current value, and the second circuit sets a magnitude of the second current to a magnitude of the first current value.

Configuration 19

The magnetic sensor according to any one of Configurations 1 to 18, wherein the first magnetic element includes a first magnetic layer, a first counter magnetic layer, and a first nonmagnetic layer provided between the first magnetic layer and the first counter magnetic layer, a direction from the first magnetic layer toward the first counter magnetic layer is along the third direction, the second magnetic element includes a second magnetic layer, a second counter magnetic layer, and a second nonmagnetic layer provided between the second magnetic layer and the second counter magnetic layer, a direction from the second magnetic layer toward the second counter magnetic layer is along the third direction, the third magnetic element includes a third magnetic layer, a third counter magnetic layer, and a third nonmagnetic layer provided between the third magnetic layer and the third counter magnetic layer, a direction from the third magnetic layer toward the third counter magnetic layer is along the third direction, the fourth magnetic element includes a fourth magnetic layer, a fourth counter magnetic layer, and a fourth nonmagnetic layer provided between the fourth magnetic layer and the fourth counter magnetic layer, and a direction from the fourth magnetic layer toward the fourth counter magnetic layer is along the third direction.

Configuration 20

An inspection device, comprising:

the magnetic sensor according to any one of Configurations 1 to 19; and a processor processing an output signal obtained from the magnetic sensor, the processor including a first lock-in amplifier that receives input of the output signal and a signal corresponding to a frequency of the alternating current component included in the first current, the first lock-in amplifier is configured to output an output signal by using, as a reference wave, the signal corresponding to the frequency of the alternating current component included in the first current.

Configuration 21

The inspection device according to Configuration 20, wherein the processor further includes a second lock-in amplifier receiving input of the output signal of the first lock-in amplifier and a signal corresponding to a frequency of a supply signal supplied toward an inspection object, and the second lock-in amplifier is configured to output an output signal by using, as a reference wave, the signal corresponding to the frequency of the supply signal supplied toward the inspection object.

According to embodiments, a magnetic sensor and an inspection device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, non-magnetic portions, magnetic members, conductive members, conductive layers, connection members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors and inspection devices practicable by an appropriate design modification by one skilled in the art based on the magnetic sensors and inspection devices described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
a sensor part including a magnetic element part, a first conductive member, and a second conductive member,
the magnetic element part including a first magnetic element, a second magnetic element, a third magnetic element, and a fourth magnetic element,
the first magnetic element including a first element portion and a first element other-portion,
the second magnetic element including a second element portion and a second element other-portion,
the third magnetic element including a third element portion and a third element other-portion,
the fourth magnetic element including a fourth element portion and a fourth element other-portion,
the first element other-portion being between the first element portion and the second element other-portion in a first direction,
the second element portion being between the first element other-portion and the second element other-portion in the first direction,
the third element other-portion being between the third element portion and the fourth element other-portion in the first direction,
the fourth element portion being between the third element other-portion and the fourth element other-portion in the first direction,
the first element other-portion being electrically connected to the second element portion,
the third element other-portion being electrically connected to the fourth element portion,
the first element portion being electrically connected to the third element portion,
the second element other-portion being electrically connected to the fourth element other-portion,
the first conductive member including a first conductive portion, a second conductive portion, a third conductive portion, a first middle portion, and a second middle portion,
a direction from the second conductive portion toward the first conductive portion being along a second direction crossing the first direction,
the third conductive portion being between the first conductive portion and the second conductive portion,
the first middle portion being between the first conductive portion and the third conductive portion,
the second middle portion being between the third conductive portion and the second conductive portion,
a direction from the first magnetic element toward the second middle portion being along a third direction crossing a plane including the first and second directions,
a direction from the third magnetic element toward the first middle portion being along the third direction,
the second conductive member including a fourth conductive portion, a fifth conductive portion, a sixth conductive portion, a third middle portion, and a fourth middle portion,
a direction from the fifth conductive portion toward the fourth conductive portion being along the second direction,
the sixth conductive portion being between the fifth conductive portion and the fourth conductive portion,
the third middle portion being between the fourth conductive portion and the sixth conductive portion,
the fourth middle portion being between the sixth conductive portion and the fifth conductive portion,
a direction from the second magnetic element toward the fourth middle portion being along the third direction,
a direction from the fourth magnetic element toward the third middle portion being along the third direction, the first conductive portion being electrically connected to the fourth conductive portion, and the second conductive portion being electrically connected to the fifth conductive portion;

a first circuit electrically connected to the third and sixth conductive portions, the first circuit being configured to supply a first current between the third conductive portion and the sixth conductive portion, the first current including an alternating current component; and a second circuit electrically connected to a first connection point and a second connection point, the first connection point being between the first element portion and the third element portion, the second connection point being between the second element other-portion and the fourth element other-portion, the second circuit being configured to supply a second current between the first connection point and the second connection point.

2. The magnetic sensor according to claim 1, further comprising:

a third circuit, the third circuit being electrically connected to a third connection point and a fourth connection point, the third connection point being between the first element other-portion and the second element portion, the fourth connection point being between the third element other-portion and the fourth element portion, and the third circuit being configured to detect a change of a potential between the third connection point and the fourth connection point.

3. The magnetic sensor according to claim 1, wherein the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction and a fourth cross length along the second direction, and the fourth length is greater than the fourth cross length.

4. The magnetic sensor according to claim 1, further comprising:

a first conductive layer;

a second conductive layer; and a fourth circuit, the first conductive layer overlapping the first and third magnetic elements in the third direction, the second conductive layer overlapping the second and fourth magnetic elements in the third direction, the first conductive layer including a first conductive layer end portion and a second conductive layer end portion, an orientation from the second conductive layer end portion toward the first conductive layer end portion being along the second direction, the second conductive layer including a third conductive layer end portion and a fourth conductive layer end portion, an orientation from the fourth conductive layer end portion toward the third conductive layer end portion being along the second direction, the first conductive layer end portion being electrically connected to the third conductive layer end portion, the second conductive layer end portion being electrically connected to the fourth conductive layer end portion, the fourth circuit being configured to supply a third current between a fifth connection point and a sixth connection point, the fifth connection point being between the first conductive layer end portion and the third conductive layer end portion, and the sixth connection point being between the second conductive layer end portion and the fourth conductive layer end portion.

5. The magnetic sensor according to claim 1, wherein the first middle portion is between the third magnetic element and a portion of the first conductive layer, the second middle portion is between the first magnetic element and an other portion of the first conductive layer, the third middle portion is between the fourth magnetic element and a portion of the second conductive layer, and the fourth middle portion is between the second magnetic element and an other portion of the second conductive layer.

6. The magnetic sensor according to claim 1, wherein a direction from the first magnetic element toward the third magnetic element is along the second direction, and a direction from the second magnetic element toward the fourth magnetic element is along the second direction.

7. The magnetic sensor according to claim 1, wherein an electrical resistance of the first magnetic element has a peak when a current supplied to the first magnetic element has a first current value, and the second circuit sets a magnitude of the second current to a magnitude of the first current value.

8. The magnetic sensor according to claim 1, wherein the first magnetic element includes a first magnetic layer, a first counter magnetic layer, and a first nonmagnetic layer provided between the first magnetic layer and the first counter magnetic layer, a direction from the first magnetic layer toward the first counter magnetic layer is along the third direction, the second magnetic element includes a second magnetic layer, a second counter magnetic layer, and a second nonmagnetic layer provided between the second magnetic layer and the second counter magnetic layer, a direction from the second magnetic layer toward the second counter magnetic layer is along the third direction, the third magnetic element includes a third magnetic layer, a third counter magnetic layer, and a third nonmagnetic layer provided between the third magnetic layer and the third counter magnetic layer, a direction from the third magnetic layer toward the third counter magnetic layer is along the third direction, the fourth magnetic element includes a fourth magnetic layer, a fourth counter magnetic layer, and a fourth nonmagnetic layer provided between the fourth magnetic layer and the fourth counter magnetic layer, and a direction from the fourth magnetic layer toward the fourth counter magnetic layer is along the third direction.

9. An inspection device, comprising:
the magnetic sensor according to claim 1; and
a processor processing an output signal obtained from the magnetic sensor,
the processor including a first lock-in amplifier that receives input of the output signal and a signal corresponding to a frequency of the alternating current component included in the first current,
the first lock-in amplifier is configured to output an output signal by using, as a reference wave, the signal corresponding to the frequency of the alternating current component included in the first current.

10. A magnetic sensor, comprising:
a sensor part including a magnetic element part and a first conductive member,
the magnetic element part including a first magnetic element, a second magnetic element, a third magnetic element, and a fourth magnetic element,
the first magnetic element including a first element portion and a first element other-portion,
the second magnetic element including a second element portion and a second element other-portion,
the third magnetic element including a third element portion and a third element other-portion,
the fourth magnetic element including a fourth element portion and a fourth element other-portion,
a direction from the first element portion toward the first element other-portion, a direction from the second element portion toward the second element other-portion, a direction from the third element portion toward the third element other-portion, and a direction from the fourth element portion toward the fourth element other-portion being along a first direction,
the first element portion being electrically connected to the second element portion,
the third element portion being electrically connected to the fourth element portion,
the first element other-portion being electrically connected to the fourth element other-portion,
the second element other-portion being electrically connected to the third element other-portion,
the first conductive member including a first conductive portion, a second conductive portion, a first portion, a second portion, a third portion, and a fourth portion,
a position in a second direction of the first portion being between a position in the second direction of the first conductive portion and a position in the second direction of the second conductive portion,
the second direction crossing the first direction,
a position in the second direction of the second portion being between the position in the second direction of the first portion and the position in the second direction of the second conductive portion,
a position in the second direction of the third portion being between the position in the second direction of the second portion and the position in the second direction of the second conductive portion,
a position in the second direction of the fourth portion being between the position in the second direction of the third portion and the position in the second direction of the second conductive portion,
a first orientation from the first magnetic element toward the first portion being along a third direction crossing a plane including the first and second directions,
a second orientation from the second magnetic element toward the second portion being a reverse of the first orientation,
a third orientation from the third magnetic element toward the third portion being a same as the first orientation, and
a fourth orientation from the fourth magnetic element toward the fourth portion being a reverse of the first orientation;
a first circuit electrically connected to the first and second conductive portions, the first circuit being configured to supply a first current between the first conductive portion and the second conductive portion, the first current including an alternating current component; and
a second circuit electrically connected to a first connection point and a second connection point, the first connection point being between the first element portion and the second element portion, the second connection point being between the third element portion and the fourth element portion, the second circuit being configured to supply a second current between the first connection point and the second connection point.

11. The sensor according to claim 10, wherein
the first conductive member further includes a first middle portion, a second middle portion, and a third middle portion,
the first middle portion is between the first magnetic element and the second magnetic element in the second direction,
the second middle portion is between the second magnetic element and the third magnetic element in the second direction, and
the third middle portion is between the third magnetic element and the fourth magnetic element in the second direction.

12. The magnetic sensor according to claim 10, wherein
the second magnetic element is between the first magnetic element and the fourth magnetic element in the second direction, and
the third magnetic element is between the second magnetic element and the fourth magnetic element in the second direction.

13. The magnetic sensor according to claim 10, wherein
the first magnetic element has a first length along the first direction, and a first cross length along the second direction,
the first length is greater than the first cross length,
the second magnetic element has a second length along the first direction, and a second cross length along the second direction,
the second length is greater than the second cross length,
the third magnetic element has a third length along the first direction, and a third cross length along the second direction,
the third length is greater than the third cross length,
the fourth magnetic element has a fourth length along the first direction, and a fourth cross length along the second direction, and
the fourth length is greater than the fourth cross length.

14. The magnetic sensor according to claim 10, further comprising:
a third circuit,
the third circuit being electrically connected to a third connection point and a fourth connection point,
the third connection point being between the first element other-portion and the fourth element other-portion, the fourth connection point being between the second element other-portion and the third element other-portion, and the third circuit being configured to detect a change of a potential between the third connection point and the fourth connection point.

15. A magnetic sensor, comprising:

a sensor part including a magnetic element part and a first conductive member,
- the magnetic element part including a first magnetic element, a second magnetic element, a third magnetic element, and a fourth magnetic element,
- the first magnetic element including a first element portion and a first element other-portion,
- the second magnetic element including a second element portion and a second element other-portion,
- the third magnetic element including a third element portion and a third element other-portion,
- the fourth magnetic element including a fourth element portion and a fourth element other-portion,
- a direction from the first element portion toward the first element other-portion, a direction from the second element portion toward the second element other-portion, a direction from the third element portion toward the third element other-portion, and a direction from the fourth element portion toward the fourth element other-portion being along a first direction,
- a second direction from the first magnetic element toward the fourth magnetic element crossing the first direction,
- a direction from the third magnetic element toward the second magnetic element being along the second direction,
- a direction from the third magnetic element toward the first magnetic element being along a third direction crossing a plane including the first and second directions,
- a direction from the second magnetic element toward the fourth magnetic element being along the third direction,
- the first element portion being electrically connected to the third element portion,
- the second element portion being electrically connected to the fourth element portion,
- the first element other-portion being electrically connected to the second element other-portion,
- the third element other-portion being electrically connected to the fourth element other-portion,
- the first conductive member including a first conductive portion, a second conductive portion, a first middle portion, and a second middle portion,
- the first middle portion being between the first conductive portion and the second conductive portion in the second direction,
- the second middle portion being between the first middle portion and the second conductive portion in the second direction,
- the first middle portion being between the third magnetic element and the first magnetic element in the third direction, and
- the second middle portion being between the second magnetic element and the fourth magnetic element in the third direction;

a first circuit electrically connected to the first and second conductive portions, the first circuit being configured to supply a first current between the first conductive portion and the second conductive portion, the first current including an alternating current component; and a second circuit electrically connected to a first connection point and a second connection point, the first connection point being between the third element portion and the first element portion, the second connection point being between the second element portion and the fourth element portion, the second circuit being configured to supply a second current between the first connection point and the second connection point.

16. The magnetic sensor according to claim 15, further comprising:

a third circuit,
- the third circuit being electrically connected to a third connection point and a fourth connection point,
- the third connection point being between the third element other-portion and the fourth element other-portion,
- the fourth connection point being between the first element other-portion and the second element other-portion, and
- the third circuit being configured to detect a change of a potential between the third connection point and the fourth connection point.

17. The magnetic sensor according to claim 15, wherein
the first magnetic element has a first length along the first direction, and a first cross length along the second direction,
the first length is greater than the first cross length,
the second magnetic element has a second length along the first direction, and a second cross length along the second direction,
the second length is greater than the second cross length,
the third magnetic element has a third length along the first direction, and a third cross length along the second direction,
the third length is greater than the third cross length,
the fourth magnetic element has a fourth length along the first direction, and a fourth cross length along the second direction, and
the fourth length is greater than the fourth cross length.

18. The magnetic sensor according to claim 15, further comprising:

a first magnetic member including a first magnetic end portion and a second magnetic end portion; and a second magnetic member including a third magnetic end portion and a fourth magnetic end portion,
- a direction from the first magnetic end portion toward the fourth magnetic end portion being along the first direction,
- the second magnetic end portion being between the first magnetic end portion and the fourth magnetic end portion in the first direction,
- the third magnetic end portion being between the second magnetic end portion and the fourth magnetic end portion in the first direction,
- the third magnetic end portion being separated from the second magnetic end portion in the first direction, and
- at least a portion of the first conductive member in the first direction being between the second magnetic end portion and the third magnetic end portion.

19. A magnetic sensor, comprising:

a sensor part including a magnetic element part, a first conductive member, and a second conductive member,
- the magnetic element part including a first magnetic element, a second magnetic element, a third magnetic element, and a fourth magnetic element, the first magnetic element including a first element portion and a first element other-portion, the second magnetic element including a second element portion and a second element other-portion, the third magnetic element including a third element portion and a third element other-portion, the fourth magnetic element including a fourth element portion and a fourth element other-portion, a direction from the first element portion toward the first element other-portion, a direction from the second element portion toward the second element other-portion, a direction from the third element portion toward the third element other-portion, and a direction from the fourth element portion toward the fourth element other-portion being along a first direction, the first element portion being electrically connected to the third element portion, the second element portion being electrically connected to the fourth element portion, the first element other-portion being electrically connected to the second element other-portion, the third element other-portion being electrically connected to the fourth element other-portion, the first conductive member including a first conductive portion, a second conductive portion, and a first portion, a position of the first portion in a second direction being between a position of the first conductive portion in the second direction and a position of the second conductive portion in the second direction, the second direction crossing the first direction, the second conductive member including a third conductive portion, a fourth conductive portion, and a second portion, a position of the second portion in the second direction being between a position of the third conductive portion in the second direction and a position of the fourth conductive portion in the second direction, the fourth magnetic element being between the second magnetic element and the first magnetic element in a third direction crossing a plane including the first and second directions, the third magnetic element being between the fourth magnetic element and the first magnetic element in the third direction, the second portion being between the second magnetic element and the fourth magnetic element in the third direction, the first portion being between the third magnetic element and the first magnetic element in the third direction, and the fourth conductive portion being electrically connected to the second conductive portion;

a first circuit electrically connected to the first and third conductive portions, the first circuit being configured to supply a first current between the first conductive portion and the third conductive portion, the first current including an alternating current component; and a second circuit electrically connected to a first connection point and a second connection point, the first connection point being between the first element portion and the third element portion, the second connection point being between the second element portion and the fourth element portion, the second circuit being configured to supply a second current between the first connection point and the second connection point.

20. The magnetic sensor according to claim 19, wherein
the first magnetic element has a first length along the first direction, and a first cross length along the second direction, the first length is greater than the first cross length, the second magnetic element has a second length along the first direction, and a second cross length along the second direction, the second length is greater than the second cross length, the third magnetic element has a third length along the first direction, and a third cross length along the second direction, the third length is greater than the third cross length, the fourth magnetic element has a fourth length along the first direction, and a fourth cross length along the second direction, and the fourth length is greater than the fourth cross length.

* * * * *